(12) United States Patent
Harada et al.

(10) Patent No.: US 8,389,949 B2
(45) Date of Patent: Mar. 5, 2013

(54) PARTICLE BEAM THERAPY SYSTEM AND ADJUSTMENT METHOD FOR PARTICLE BEAM THERAPY SYSTEM

(75) Inventors: Hisashi Harada, Chiyoda-ku (JP); Takaaki Iwata, Chiyoda-ku (JP)

(73) Assignee: Mitsusbishi Electric Corporation, Chiyoda-Ku, Tokyo (JP)

( * ) Notice: Subject to any disclaimer, the term of this patent is extended or adjusted under 35 U.S.C. 154(b) by 304 days.

(21) Appl. No.: 12/864,612

(22) PCT Filed: Jun. 9, 2009

(86) PCT No.: PCT/JP2009/060532
§ 371 (c)(1),
(2), (4) Date: Jul. 26, 2010

(87) PCT Pub. No.: WO2010/143268
PCT Pub. Date: Dec. 16, 2010

(65) Prior Publication Data
US 2011/0121195 A1 May 26, 2011

(51) Int. Cl.
*H01J 1/50* (2006.01)
(52) U.S. Cl. ............ 250/396 ML; 250/396 R; 250/398; 250/492.1; 250/492.3; 250/505.1
(58) Field of Classification Search .............. 250/396 R, 250/398, 396 ML, 492.1, 492.3, 505.1
See application file for complete search history.

(56) References Cited

U.S. PATENT DOCUMENTS

| | | | |
|---|---|---|---|
| 6,218,675 B1* | 4/2001 | Akiyama et al. | 250/492.3 |
| 6,730,921 B2* | 5/2004 | Kraft | 250/492.1 |
| 7,345,291 B2* | 3/2008 | Kats | 250/492.22 |
| 7,547,901 B2* | 6/2009 | Guertin et al. | 250/492.3 |
| 7,560,717 B2* | 7/2009 | Matsuda et al. | 250/505.1 |
| 2002/0030164 A1* | 3/2002 | Akiyama et al. | 250/492.1 |
| 2003/0141460 A1* | 7/2003 | Kraft | 250/492.1 |
| 2003/0183779 A1* | 10/2003 | Norimine et al. | 250/492.3 |
| 2007/0114455 A1* | 5/2007 | Naito et al. | 250/492.21 |
| 2007/0114473 A1* | 5/2007 | Matsuda et al. | 250/505.1 |

FOREIGN PATENT DOCUMENTS

| | | |
|---|---|---|
| EP | 0858080 A1 | 8/1998 |
| EP | 1348465 A1 | 10/2003 |
| EP | 1358908 A1 | 11/2003 |

(Continued)

OTHER PUBLICATIONS

Supplementary European Search Report dated May 15, 2012, 8 pps.

(Continued)

*Primary Examiner* — Michael Logie
(74) *Attorney, Agent, or Firm* — Buchanan Ingersoll & Rooney PC

(57) ABSTRACT

The objective is to obtain a particle beam therapy system, the irradiation flexibility of which is high and that can reduce the amount of irradiation onto a normal tissue. There are provided a scanning electromagnet that performs scanning and outputting in such a way that a supplied charged particle beam is formed in a three-dimensional irradiation shape based on a treatment plan; and deflection electromagnets that switch the orbits for the charged particle beam in such a way that the charged particle beam with which scanning and outputting are performed by the scanning electromagnet reaches an isocenter through a single beam orbit selected from a plurality of beam orbits established between the isocenter and the scanning electromagnet. The distance between the scanning electromagnet and the isocenter is made long.

10 Claims, 12 Drawing Sheets

FOREIGN PATENT DOCUMENTS

| | | |
|---|---|---|
| JP | 5-111540 A | 5/1993 |
| JP | 5-288900 | 11/1993 |
| JP | 8-257148 A | 10/1996 |
| JP | 3178381 B2 | 6/2001 |
| JP | 2002-113118 A | 4/2002 |
| JP | 2003-528659 A | 9/2003 |
| JP | 2007-89928 A | 4/2007 |
| JP | 2007-132902 A | 5/2007 |
| JP | 2009-39353 A | 2/2009 |
| JP | 2009-119123 A | 6/2009 |
| WO | WO 01/66187 A1 | 9/2001 |

OTHER PUBLICATIONS

Kats et al, "A Simple, Compact, Flat System for the Irradiation of a Lying Patient with a Proton Beam from Different Directions", Instruments for Ecology Medicine and Biology, Instruments and Experimental Techniques, vol. 39, No. 1, 1996, pp. 132-134.

Kats, "Planar System Replacing Gantry for Protons and Carbon Ions Beams Transportation", European Particle Accelerator Conference, EPAC, Jan. 1, 1998, pp. 2362-2364.

International Search Report (PCT/ISA/210) dated Aug. 4, 2009.

\* cited by examiner

PARTICLE BEAM THERAPY SYSTEM AND ADJUSTMENT METHOD FOR PARTICLE BEAM THERAPY SYSTEM

TECHNICAL FIELD

The present invention relates to a particle beam therapy system that irradiates a proton beam or a heavy ion beam for the purpose of treating a cancer or the like and to an adjustment method for a particle beam therapy system; the present invention relates particularly to a particle beam therapy system utilizing a scanning-type irradiation method such as a spot-scanning method or a raster-scanning method.

BACKGROUND ART

When an X ray or a gamma ray is irradiated from the outside of a body, the dose becomes maximum in the vicinity of the surface of the body, and then the dose decreases as the depth increased. Accordingly, when it is tried to apply a sufficient dose to a tumor volume located in a deep position, there is caused larger damage to normal cells located at a shallower position than the tumor volume. In contrast, in the case of particle-beam irradiation, irradiation energy determines the depth of a position, in a body, at which a particle beam can arrive, and there exists a phenomenon referred to as the "Bragg peak" phenomenon in which the particle beam stops at nearly the same position as the foregoing position after emitting its energy rapidly. Therefore, by utilizing this phenomenon and appropriately adjusting the energy of a particle beam, it is made possible to kill and wound only tumor cells while suppressing the effect against normal cells existing between the surface of a body and a tumor volume. As a result, because a particle beam can intensively be irradiated onto a tumor volume, the particle-beam irradiation method is expected as a therapy method that does not impose a great deal of physical burden on a patient and less strenuous on the elderly.

On the other hand, particle-beam irradiation requires a large beam source such as an accelerator; therefore, because, unlike an X-ray source, the beam source per se cannot readily be moved, various proposals have been made in order to perform irradiation onto a diseased site at an appropriate angle. For example, in the case where a tumor in a brain or in an eyeball is treated, it is common that the treatment is performed in a horizontal irradiation chamber where a patient is seated in a chair-type patient holding apparatus, and a charged particle beam is horizontally irradiated. There has been proposed a chair-type patient holding apparatus, for radiation therapy, in which designing is performed in such a way that a charged particle beam is irradiated onto a target irradiation position referred to as an isocenter, and positioning of a patient is performed in such a way that the chair-type patient holding apparatus is moved while an X-ray radiographic image is viewed (for example, refer to Patent Document 1). There has been proposed a chair-type patient holding apparatus in which there is provided an adjustment apparatus capable of moving a patient to the center of rotation (for example, refer to Patent Document 2).

In the case of particle-beam irradiation, even though, as described above, a Bragg peak occurs, a particle beam irradiated from the outside of a body affects the surface of the body as well, to some extent. Thus, in a particle beam therapy system, in order to avoid irradiation onto an important normal tissue, it is required that the irradiation angle can appropriately be set in accordance with a diseased site. In addition, there has been proposed a multi-port irradiation method in which irradiation onto a tumor volume is performed from a plurality of directions; its effect of reducing irradiation onto a normal tissue is known.

However, in the case of a horizontal-irradiation method utilizing a conventional chair-type patient holding apparatus, it is required to change the posture of the whole chair-type patient holding apparatus with a patient supported thereon, when irradiation angle is changed; therefore, there has been a problem that a burden is imposed on the patient. For example, when the chair-type patient holding apparatus is slanted forward or laterally, a great deal of burden is imposed, especially on an aged patient.

Accordingly, there is well known a method in which, in order to realize a high-flexibility irradiation angle, not a fixed-port-irradiation type but a rotating-irradiation-type particle beam therapy system referred to as a rotating gantry is utilized in combination with a bed-type patient holding apparatus. However, this method requires a large system; thus, there has been problems that a great deal of initial cost (introduction cost) and running cost is required, that installation thereof needs a large space, and the like. A particle beam therapy system equipped with a rotating gantry is commonly utilized in proton-beam therapy; however, in the case where a heavy ion such as a carbon ion is utilized as a charged particle, the curvature radius at a time when a beam orbit is bent is large and hence a large electromagnet is required to be rotated; thus, systemization becomes further difficult. Even though multi-port irradiation can be performed by use of a rotating gantry, the irradiation apparatus is driven to rotate along with the rotating gantry when the irradiation angle is changed; therefore, there has been a problem that the irradiation angle cannot be changed unless an engineer enters the irradiation chamber and confirms that the irradiation apparatus and a patient do not collide with each other.

Therefore, there has been proposed a beam irradiation apparatus where, in order to realize flexibility in the irradiation angle without utilizing a rotating gantry, the irradiation nozzle and the scanning electromagnet are moved for each of a plurality of beam orbits defined by a deflection electromagnet (for example, refer to Patent Documents 3 and 4).

Here, in the irradiation system of a particle beam therapy system, there are required roughly two functions below. One function is to irradiating a charged particle beam onto a desired position at a desired angle, and the other function is to form an irradiation shape for selectively performing irradiation onto an irradiation subject such as a tumor. Particle beam therapy systems are divided roughly into two types, depending on the method for realizing the function of forming an irradiation shape. One of them is referred to as a broad-beam irradiation type in which irradiation onto an irradiation region is performed at once by use of an irradiation nozzle configured with a wobbler magnet, a scatterer, a range modulator, a patient collimator, a patient bolus, and the like; the other one is referred to as a scanning irradiation type in which irradiation onto an irradiation region is performed stepwise by scanning small irradiation regions with a scanning electromagnet or the like. In either types, a particle beam heads for an irradiation subject from an irradiation nozzle or a scanning electromagnet in such a way as to spread in a divergence direction; therefore, when the distance between the irradiation subject and the irradiation nozzle or the scanning electromagnet is short, the divergence angle becomes large. As a result, even in the case where irradiation onto the same irradiation subject is performed, the area of a body surface through which a charged particle beam passes becomes small in comparison with a case where the divergence angle is small; thus, the irradiation density on the body surface becomes large, whereby damage to the body surface, which is a normal tissue, increases.

PRIOR ART REFERENCE

Patent Document

[Patent Document 1] Japanese Patent Application Laid-Open No. 2007-89928 (paragraph 0012 and FIG. 1)
[Patent Document 2] Japanese Patent Application Laid-Open No. H5-111540 (paragraph 0018 and FIG. 3)
[Patent Document 3] Japanese Patent Application Laid-Open No. 2002-113118 (paragraph 0013 and FIG. 1)
[Patent Document 4] Japanese Patent Application Laid-Open No. 2003-528659 (paragraph 0055 and FIG. 6)

DISCLOSURE OF THE INVENTION

Problems to be Solved by the Invention

In the case where, as described above, an irradiation nozzle or a scanning electromagnet is moved in accordance with a beam orbit defined by a deflection electromagnet, the irradiation nozzle or the scanning electromagnet is disposed at the downstream side of the deflection electromagnet. As a result, the distance between the irradiation subject and the irradiation nozzle or the scanning electromagnet needs to be shortened. Accordingly, the divergence angle of a particle beam becomes large; therefore, there has been a problem that the irradiation density on a body surface increases and hence the amount of irradiation onto a normal tissue is enlarged. Furthermore, there has been a problem that, due to the necessity of moving a heavy irradiation nozzle or scanning electromagnet, the system becomes complicated.

The present invention has been implemented in order to solve the foregoing problems; the objective thereof is to obtain a particle beam therapy system, the irradiation flexibility of which is high and that can reduce the amount of irradiation onto a normal tissue.

Means for Solving the Problems

A particle beam therapy system according to the present invention is provided with a scanning electromagnet that performs scanning in such a way that a supplied charged particle beam is formed in a three-dimensional irradiation shape based on a treatment plan; and a deflection electromagnet that switches orbits for a charged particle beam in such a way that the charged particle beam with which scanning is performed by the scanning electromagnet reaches an isocenter through a single beam orbit selected from a plurality of beam orbits established between the isocenter and the scanning electromagnet.

Moreover, an adjustment method for a particle beam therapy system according to the present invention includes a step of providing a beam measurement unit that sets a beam orbit and measures the actual irradiation position coordinates of a charged particle beam in accordance with the set beam orbit; a step of reading a plurality of irradiation control values that are different from one another; a step of actually irradiating a charged particle beam in accordance with the read irradiation control values and measuring the actual irradiation position coordinates, at the isocenter, of the charged particle beam; and a step of setting unknown parameters in the inverse-map mathematical expression model, based on a combination of a plurality of measurement results for the measured actual irradiation position coordinates and the plurality of irradiation control values.

Still moreover, a particle beam therapy system according to the present invention is provided with an inverse map calculation unit that performs a step of reading a plurality of irradiation control values that are different from one another; a step of measuring the actual irradiation position coordinates, at the isocenter, of a charged particle beam that has been actually irradiated in accordance with the read irradiation control values; and a step of setting unknown parameters in the inverse-map mathematical expression model, based on a combination of a plurality of measurement results for the measured actual irradiation position coordinates and the plurality of irradiation control values.

Advantage of the Invention

In a particle beam therapy system according to the present invention, a scanning electromagnet is disposed at the upstream side of a deflection electromagnet for switching a beam orbit; therefore, by making the divergence distance of a charged particle beam longer, there can be obtained a particle beam therapy system, the irradiation flexibility of which is high and that can reduce the amount of irradiation onto a normal tissue.

In an adjustment method for a particle beam therapy system according to the present invention, a data string of irradiation control values is read for each beam orbit, and actual irradiation with a charged particle beam is performed; then, through the combination of the data string of actual irradiation position coordinates of a charged particle beam at the isocenter and the data string of the irradiation control values, unknown parameters of an inverse map model for control values are set based on the irradiation position coordinates; therefore, there can be obtained a particle beam therapy system that enables accurate irradiation, whatever orbit is selected.

BEST MODE FOR CARRYING OUT THE INVENTION

Embodiment 1

Figure 1:
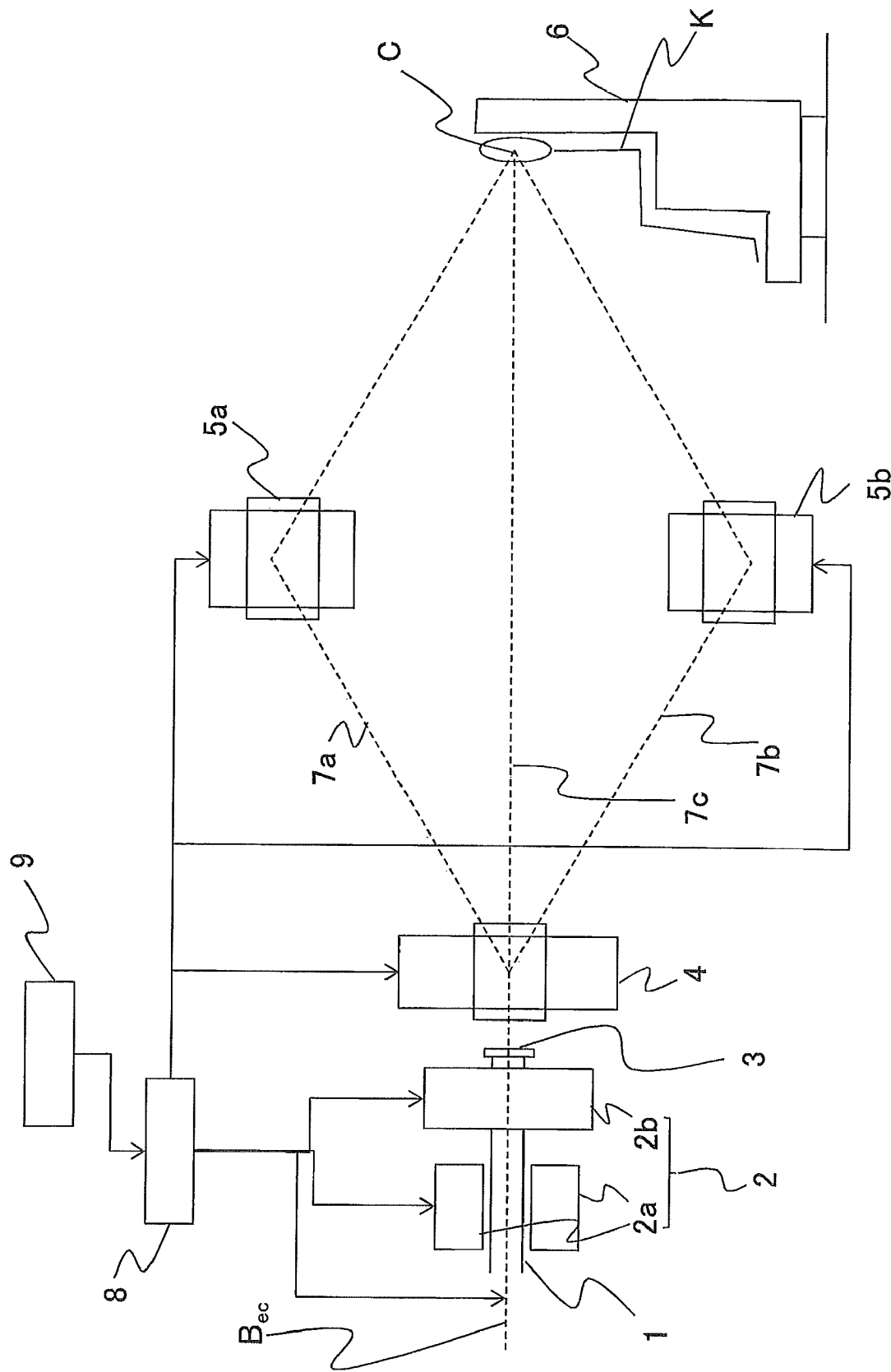
FIG. 1 is a diagram illustrating the configuration of a particle beam therapy system according to Embodiment 1 of the present invention.
Figure 2:
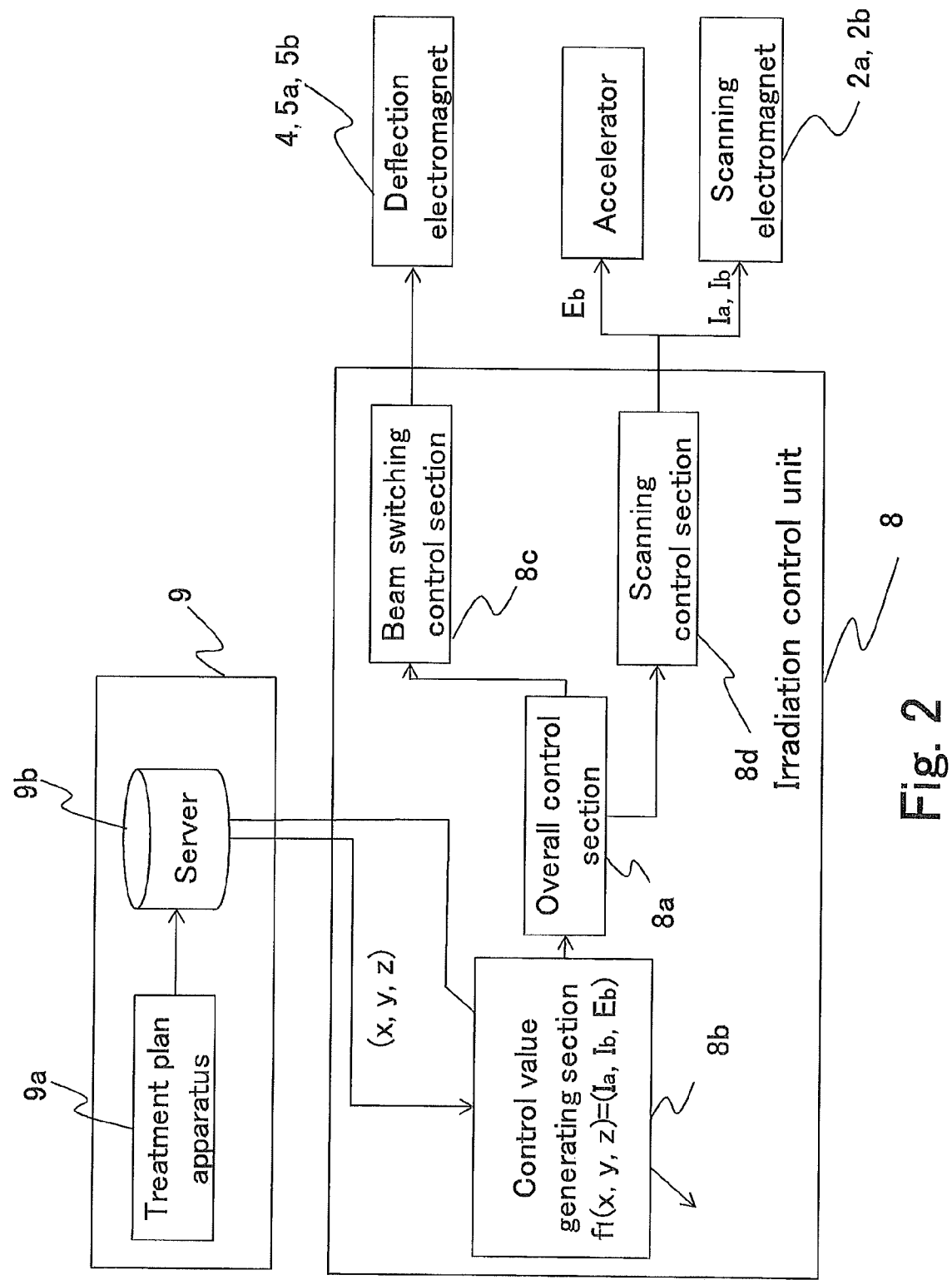
FIG. 2 is a block diagram illustrating the functions of a particle beam therapy system according to Embodiment 1 of the present invention.

Embodiment 1 of a particle beam therapy system according to the present invention will be explained below. FIGS. 1 and 2 are diagrams for explaining a particle beam therapy system according to Embodiment 1 of the present invention. FIG. 1 is a diagram illustrating the overall configuration of a particle beam therapy system; FIG. 2 is a block diagram illustrating the function of a particle beam therapy system. As illustrated in FIG. 1, the particle beam therapy system includes a beam transport duct 1 for transporting an accelerated charged particle beam $B_{ec}$ without diffusing it; a scanning electromagnet 2 (2a and 2b) that is disposed outside the beam transport duct 1 in such a way that the beam transport duct 1 are inserted therein, and that performs scanning with the transported charged particle beam $B_{ec}$; a beam outlet window 3 for extracting the charged particle beam $B_{ec}$ with which scanning has been performed; a deflection electromagnet 4 that is disposed at the downstream side of the scanning electromagnet 2 and switches the orbit of the charged particle beam $B_{ec}$, extracted through the beam outlet window 3, over to a plurality of beam orbits (7a, 7b, and 7c) that follows the foregoing orbit; deflection electromagnets 5 (5a and 5b, not required in 7c) that deflect the charged particle beam $B_{ec}$ to an isocenter C, which is a final target irradiation position, in the respective beam orbits (7a, 7b, and 7c); and a chair-type patient holding apparatus 6 for holding a patient K in a sitting posture.

The particle beam therapy system is provided with an irradiation control unit 8 that controls the operations of the scanning electromagnet 2 (2a and 2b), the deflection electromagnet 4, and the deflection electromagnet 5 (5a and 5b), and the operation of an unillustrated charged particle beam supply unit situated at the upstream side thereof so as to adjust the kinetic energy of the charged particle beam $B_{ec}$, in accordance with an irradiation method given in a commanding manner by an irradiation plan commanding unit 9.

Next, control of respective units will be explained with reference to FIG. 2. In Embodiment 1, the irradiation plan commanding unit 9 is an apparatus separated from a particle beam therapy system and includes a treatment plan apparatus 9a that creates an appropriate treatment plan for a diseased site and a server 9b that holds various data items and outputs data items such as a specific irradiation angle and an irradiation shape in accordance with a created treatment plan. In the irradiation control unit 8 of the particle beam therapy system according to Embodiment 1, irradiation control is performed mainly by an overall control section 8a in accordance with data such as the point sequence data of target irradiation coordinates (x, y, z) created based on an irradiation angle (beam orbit) and an irradiation shape outputted from the irradiation plan commanding unit 9. In order to realize irradiation onto the coordinates (x, y, z) for forming an irradiation shape specified at the isocenter C, a control value generating section 8b of the irradiation control unit 8 selects a function $f_1$ (x, y, z) for calculating, from the target irradiation coordinates (x, y, z), control values ($I_a$, $I_b$, $E_b$) for the scanning electromagnets 2a and 2b and for the energy (kinetic energy of a charged particle) of the charged particle beam $B_{ec}$, in accordance with the irradiation angle (beam orbit 7a, 7b, or 7c). After that, the control value generating section 8b calculates the control values ($I_a$, $I_b$, $E_b$) from the target irradiation coordinates (x, y, z), by use of the function $f_1$ (the function $f_1$ may be selected from a look-up table) selected in accordance with the beam orbit (7a, 7b, or 7c); the calculated control values ($I_a$, $I_b$, $E_b$) are outputted to the overall control section 8a; finally, the scanning electromagnet 2 (2a and 2b) and the accelerator are controlled. In this situation, the target irradiation coordinates (x, y, z) are coordinates in the coordinate system configured of coordinate axes x and y in a plane perpendicular to the center axis of a beam orbit in the vicinity of the isocenter, which is an irradiation subject, and a coordinate axis z along the irradiation depth direction. The control values include control values for the scanning electromagnet 2 (2a and 2b) for realizing an irradiation shape and control values for the accelerator that determines the energy of the charged particle beam $B_{ec}$; in particular, the three-dimensional control values ($I_a$, $I_b$, $E_b$) will be referred to as irradiation control values, hereinafter.

In order to set the beam orbit (7a, 7b, or 7c), the overall control section 8a outputs, to a beam switching control section 8c, control command signals for the deflection electromagnets 4, 5a, and 5b. The irradiation control values ($I_a$, $I_b$, $E_b$) created by the control value generating section 8b are outputted to the scanning electromagnets 2a and 2b and the accelerator, which is a charged particle beam supply unit, respectively. Complementarily speaking, the control values for the scanning electromagnet 2a and 2b are specifically a current value, a current value that are calculated in a compensating manner taking a hysteresis into account, or a setting value of magnetic field intensity; the control value for the accelerator is specifically the target kinetic energy of a charged particle or the like.

In addition, although unillustrated, the chair-type patient holding apparatus 6 can rotate on the rotation axle that passes through the isocenter C; the rotation angle, the position such as the height, and the posture thereof can also be controlled by the overall control section 8a.

Next, the operation will be explained. The charged particle beam $B_{ec}$ accelerated by an unillustrated accelerator is introduced to the beam transport duct 1 by way of an unillustrated transport system. The charged particle beam $B_{ec}$ introduced to the beam transport duct 1 is scanning-controlled by the scanning electromagnet 2 (e.g., x-direction scanning by 2a, and y-direction scanning by 2b) to which the control values ($I_a$, $I_b$) are inputted in such a way that there is realized an irradiation shape for performing irradiation onto an irradiation subject such as a tumor with a selective and desired dose. The scanning-controlled charged particle beam $B_{ec}$ is extracted through the beam outlet window 3, and then introduced to the deflection electromagnet 4 for switching the beam orbit. The charged particle beam $B_{ec}$ introduced to the deflection electromagnet 4 is deflected by the deflection electromagnet 4 in accordance with the set orbit. In this situation, in the case of the orbit 7a, the charged particle beam $B_{ec}$ is deflected upward in FIG. 1; in the case of the orbit 7b, the charged particle beam $B_{ec}$ is deflected downward in FIG. 1; in the case of the orbit 7c, the charged particle beam $B_{ec}$ goes straight without being deflected. In the case of the orbit 7a, the deflection electromagnet 5a operates; the charged particle beam $B_{ec}$ is deflected downward and irradiated to the isocenter C from upper side thereof. In the case of the orbit 7b, the deflection electromagnet 5b operates; the charged particle beam $B_{ec}$ is deflected upward and irradiated to the isocenter C from lower side thereof. In the case of the orbit 7c, the charged particle beam $B_{ec}$ is irradiated horizontally toward the isocenter C.

In other words, the scanning electromagnets 2a and 2b for forming the charged particle beam $B_{ec}$ in a three-dimensional irradiation shape are arranged at the upstream side of the deflection electromagnets 4, 5a, and 5b; thus, the charged particle beam $B_{ec}$ diverges through such a long distance as that from the beam outlet window 3 to the isocenter C, even in the shortest case. For example, in the case where the size of an irradiation region at the isocenter is 10 cm, the divergence angle becomes 2.3° when the distance between the beam outlet window 3 and the isocenter C is 5 m; the divergence angle becomes 1.1° when the distance between the beam outlet window 3 and the isocenter C is 10 m. In contrast, in the case where, as disclosed in Patent Documents 3 and 4, a scanning means is disposed at the downstream side of the deflection electromagnet, when the distance between the position where the divergence begins and the isocenter C is made long, the apparatus becomes large; therefore, making the distance long is substantially difficult. Accordingly, for example, in the case where the distance becomes 1 m or 50 cm, the divergence angle is enlarged up to 11° or 23°, respectively. In this case, for example, in the case where a particle beam is irradiated onto a diseased site situated 10 cm deep from a body surface, when, as Embodiment 1, the distance is 10 m or 5 m, the irradiation density ratio (body-surface irradiation density/diseased-site irradiation density) at the body surface is 1.0; however, when the distance is 1 m or 50 cm, the irradiation density ratio increases up to 1.2 or 1.6, respectively, whereby the damage to a normal tissue is enlarged.

In the particle beam therapy system according to Embodiment 1, because it is not required to enlarge the angles at which the scanning electromagnets 2a and 2b bent a beam, the sizes of the scanning electromagnets can be reduced, whereby the power consumption can also be reduced.

As described above, the particle beam therapy system according to Embodiment 1 is configured in such a way as to include the scanning electromagnets 2a and 2b that performs scanning with a supplied charged particle beam $B_{ec}$ in such a way that the charged particle beam $B_{ec}$ is formed in a three-dimensional irradiation shape based on a treatment plan; and the deflection electromagnets 4, 5a, and 5b that switch the orbits for the charged particle beam $B_{ec}$ in such a way that the charged particle beam $B_{ec}$ with which scanning is performed by the scanning electromagnets 2a and 2b reaches the isocenter C through a single beam orbit selected from a plurality of beam orbits 7a, 7b, and 7c established between the isocenter C and the scanning electromagnets 2a and 2b. As a result, the charged particle beam $B_{ec}$ begins to diverge at a position that is far away from the isocenter, which is an irradiation subject; thus, the divergence angle can be suppressed. Therefore, the irradiation flexibility is raised, and the irradiation density on a body surface is prevented from increasing, so that the irradiation amount on a normal tissue can be reduced.

That is to say, by arranging the deflection electromagnets 4 and 5 at the downstream side of the scanning electromagnet 2, which is conventionally disposed at the most downstream side, there can be obtained a compact particle beam therapy system having high flexibility in the irradiation angle, without utilizing a large rotating gantry. Because of the high flexibility in the irradiation angle, it is not required to change the posture of a patient (the posture may be changed, but not required to be changed largely in comparison with horizontal irradiation performed by means of a conventional fixed port); therefore, there can be obtained a particle beam therapy system that imposes little burden on an aged patient. Moreover, there can be obtained a compact particle beam therapy system having high irradiation flexibility, without utilizing a large rotating gantry or moving the scanning electromagnet.

In particular, the particle beam therapy system is configured in such a way as to include the irradiation control unit 8 that converts irradiation position coordinates (x, y, z) for forming a three-dimensional irradiation shape by use of a function $f_1$ set in accordance with a selected beam orbit 7a, 7b, or 7c, and controls the energy of the scanning electromagnets 2a and 2b and a charged particle beam $B_{ec}$ by utilizing irradiation control values ($I_a$, $I_b$, $E_b$) obtained through the conversion.

The specific method of creating control values will be described in detail in Embodiment 2; even in the case where there is adopted a complicated system where the scanning electromagnet having a function of forming an irradiation shape is not disposed at the most downstream side and there exists a plurality of beam orbits, there can be created control values for realizing accurate irradiation onto target irradiation coordinates. Accordingly, whatever orbit is selected, accurate irradiation can be performed; therefore, it is made possible for the arrangement of irradiation system apparatuses to have flexibility, while keeping the irradiation accuracy high.

Furthermore, the deflection electromagnets that are provided at the downstream side of the scanning electromagnet 2 and switch the beam orbits include the beam switching electromagnet 4, which is a first deflection electromagnet, that deflects a charged particle beam $B_{ec}$ scanning-outputted from the scanning electromagnet 2, in accordance with a selected orbit (7a, 7b, or 7c); and the deflection electromagnets 5a and 5b (although not required for the orbit 7c, it is basically described that the deflection electromagnet is provided for each beam orbit), which configure a second deflection electromagnet, that are provided, at the downstream side of the beam switching electromagnet 4, for each of a plurality of beam orbits and deflect the charged particle beam $B_{ec}$ deflected by the beam switching electromagnet 4 toward the isocenter C. As a result, nothing is to be moved when the beam orbit is changed; thus, the irradiation angle can readily be switched.

Moreover, according to Embodiment 1, it is not required to prepare a plurality of scanning electromagnets 2 in accordance with a plurality of beam orbits or to make the scanning electromagnet movable. Still moreover, unlike a method utilizing a rotating gantry, there exists no irradiation unit to be driven in the vicinity of a patient when the irradiation angle is changed; therefore, it is not required that each time the irradiation angle is changed, an engineer enters the irradiation chamber, whereby there can be obtained a particle beam therapy system in which multi-port irradiation is remotely performed.

With regard to the particle beam therapy system according to Embodiment 1, there is illustrated an example where, as the deflection electromagnet 5, the deflection electromagnets 5a and 5b are arranged at the top and bottom positions in the plane of the paper, and the deflection electromagnet 4 changes the orbit only upward and downward in the plane of the paper; however, the present invention is not limited thereto. For example, the number of orbits heading upward and downward may be changed, or the deflection electromagnets 5a and 5b may be arranged at any positions on the circumferential direction of the orbit 7. In this case, the beam switching deflection electromagnet 4 may appropriately be rotated on the orbit 7c, in accordance with a set beam orbit.

In Embodiment 1, the method of calculating the function $f_1$ has not been particularly described; however, the function $f_1$ can be set by performing a simulation for each beam orbit in accordance with the natures of the deflection electromagnets 4 and 5. In addition, as Embodiment 2 described later, there may be utilized an inverse-map mathematical expression model created based on an actually measured value.

Embodiment 2

Figure 3:
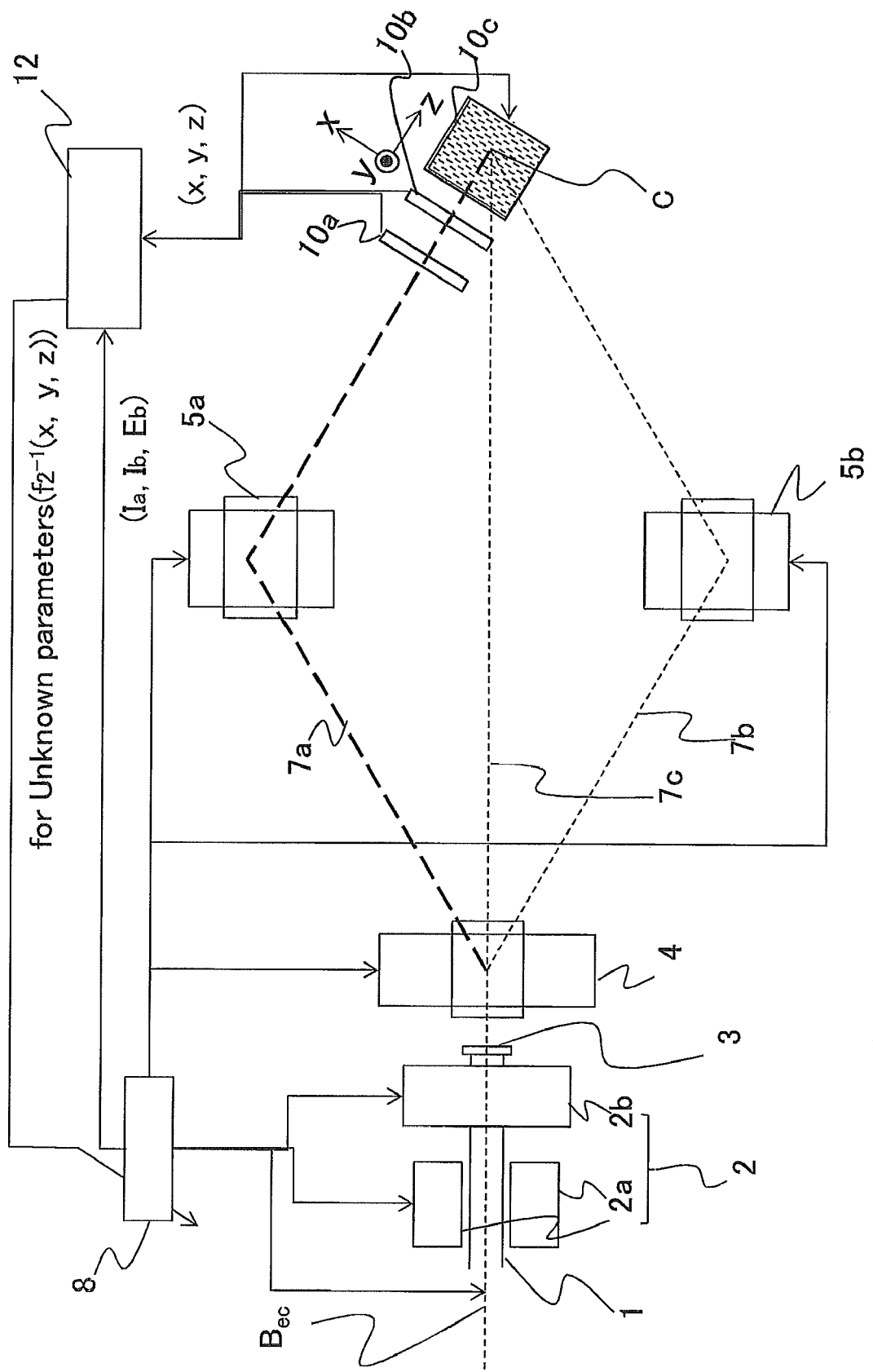
FIG. 3 is a diagram illustrating the configuration of a particle beam therapy system according to Embodiment 2 of the present invention.
Figure 4:
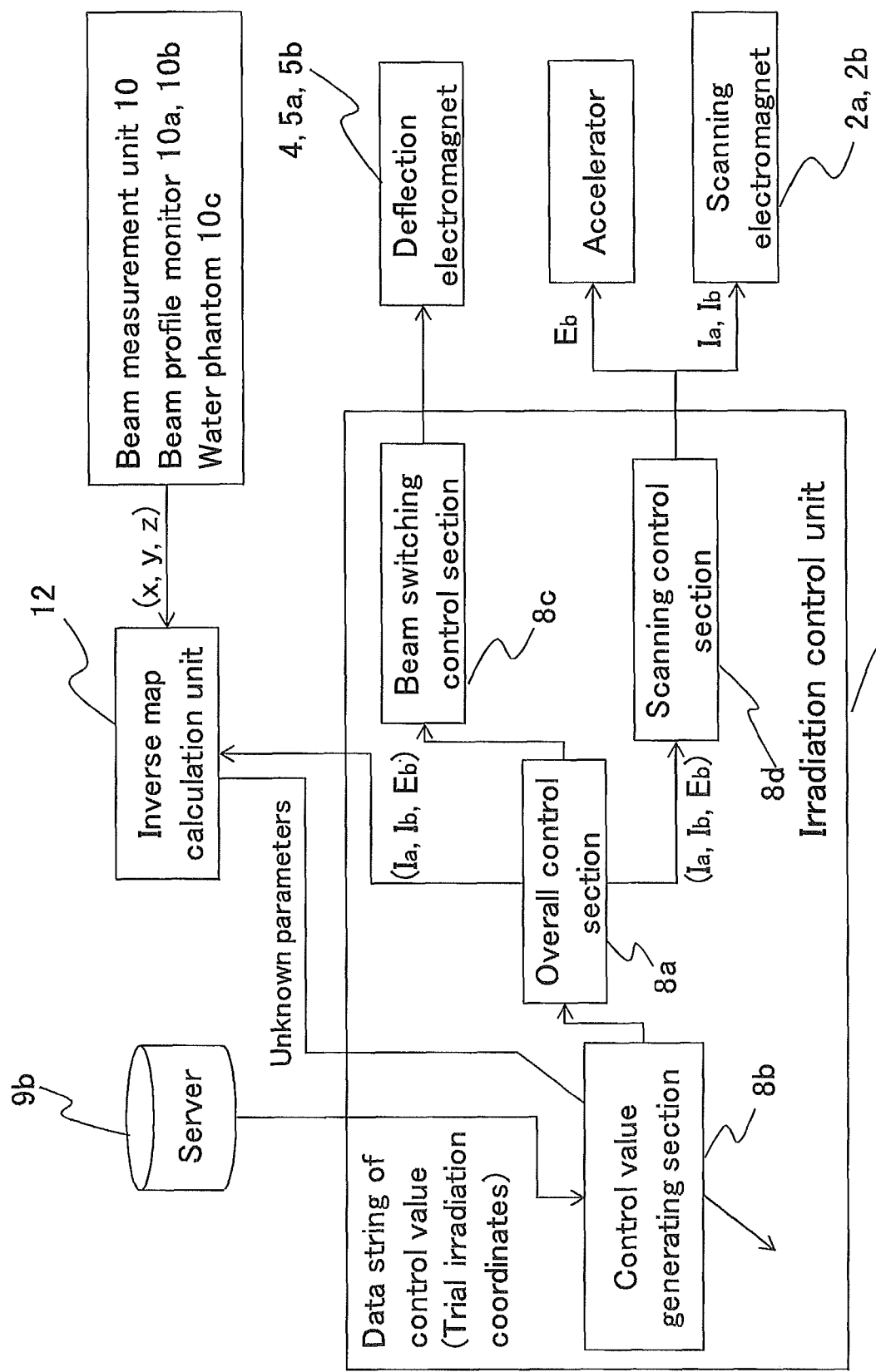
FIG. 4 is a block diagram illustrating the functions of a particle beam therapy system according to Embodiment 2 of the present invention.
Figure 5:
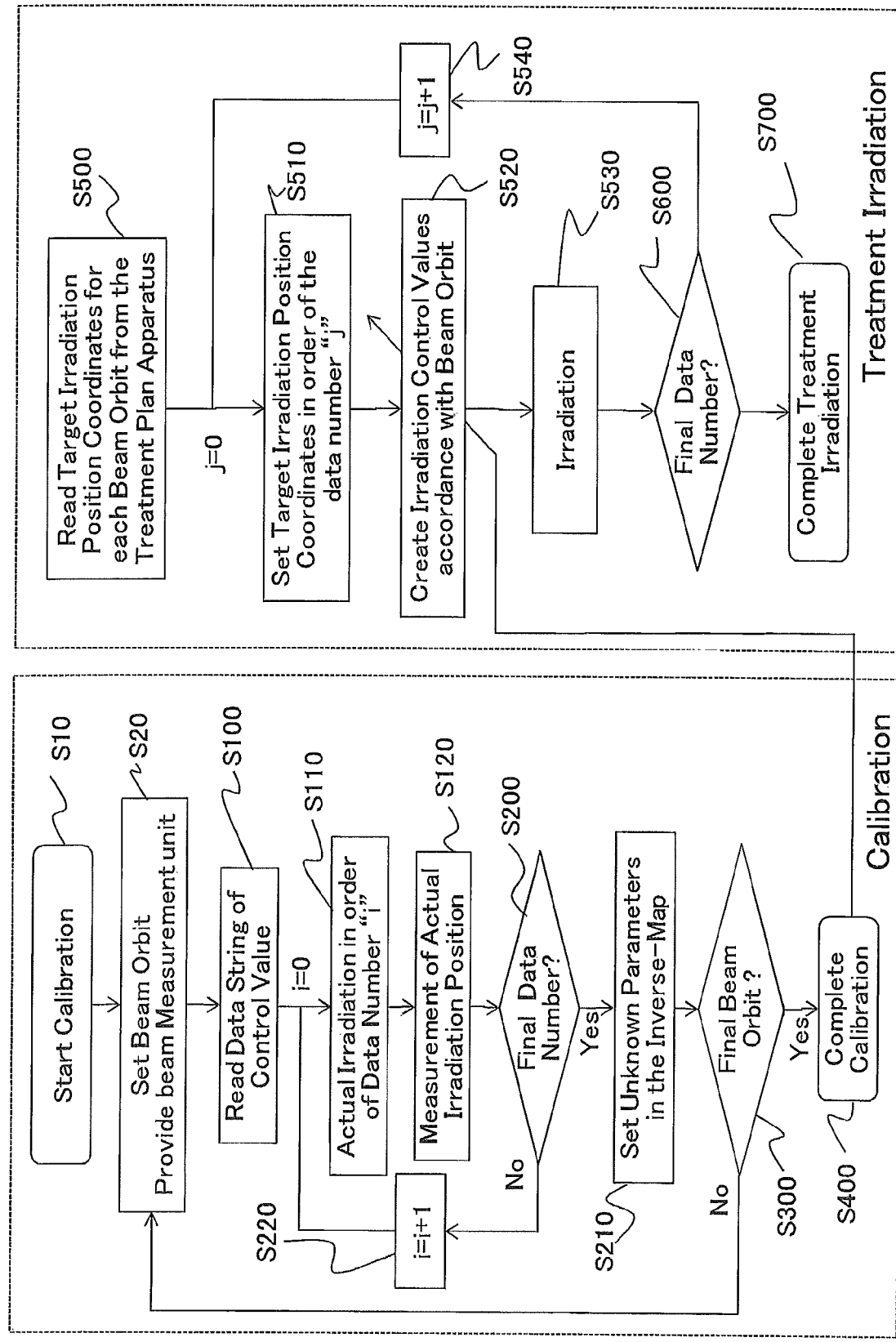
FIG. 5 is a flowchart representing an adjustment method for a particle beam therapy system according to Embodiment 2 of the present invention.

A particle beam therapy system and an adjustment method for a particle beam therapy system according to Embodiment 2 of the present invention will be explained below. FIGS. 3 and 4, and FIG. 5 are diagrams and a flowchart, respectively, for explaining a particle beam therapy system and an adjustment method for a particle beam therapy system according to Embodiment 2 of the present invention; FIG. 3 is a diagram illustrating the overall configuration of a particle beam therapy system; FIG. 4 is a block diagram illustrating the function of a particle beam therapy system; FIG. 5 is a flowchart representing an adjustment method for a particle beam therapy system. In the particle beam therapy system according to Embodiment 2, there will be described in detail the fact that, as a function of calculating, in accordance with a beam orbit, three-dimensional irradiation control values $(I_a, I_b, E_b)$ from the point sequence data of target irradiation coordinates (x, y, z) for forming an irradiation shape, an inverse-map mathematical expression model $f_2^{-1}$ on an actually measured value is utilized and the function of setting unknown parameters in the inverse-map mathematical expression model. Other items are the same as those in Embodiment 1. In FIG. 3, there are omitted the patient K and the chair-type patient holding apparatus 6 that are not utilized for explaining the adjustment of the particle beam therapy system.

In the particle beam therapy system according to Embodiment 2, there are provided a beam measurement unit 10 (beam profile monitors 10a and 10b and a water phantom 10c) for measuring the irradiation position (coordinates (x, y) in a plane perpendicular to the center of a beam orbit and a depth Z in parallel with the beam orbit) of a particle beam $B_{ec}$ in the vicinity of the isocenter C; and an inverse map calculation unit 12 that sets unknown parameters in the inverse-map mathematical expression model $f_2^{-1}$ for each beam orbit, based on irradiation control values and actually measured values.

The beam measurement unit 10 is provided for each beam orbit; in FIG. 3, there is illustrated a case where an irradiation shape in the beam orbit 7a is measured. The beam measurement unit 10 is disposed basically in such a way that a line (the Z axis in the beam measurement unit 10) connecting the respective centers of 10a, 10b, and 10c passes through the center of the beam orbit; the water phantom is disposed in such a way as to incorporate the isocenter C so that the whole irradiation area can be covered. The beam profile monitors 10a and 10b are arranged at respective positions that are at the upstream side of the water phantom in the beam orbit and that are different from one another in the depth (in the z direction) along the beam orbit, and there is measured the position (it is assumed that the direction perpendicular to the z direction in the plane of the paper is the x direction and the direction perpendicular to the plane of the paper is the y direction) of a beam in a plane perpendicular to the beam orbit.

In FIGS. 3 and 4, there is illustrated a case where the inverse map calculation unit 12 is disposed separated from the irradiation control unit 8 and the irradiation plan commanding unit 9; the unknown parameters, in the inverse-map mathematical expression model $f_2^{-1}$, calculated by the inverse map calculation unit 12 are stored in the data server 9b; and in the case of an actual treatment, the control value generating section 8b calls and utilizes the unknown parameters, in the inverse-map mathematical expression model $f_2^{-1}$, stored in the data server 9b. However, the inverse map calculation unit 12 may be incorporated in the irradiation control unit 8 or the irradiation plan commanding unit 9; as long as the unknown parameters in the inverse-map mathematical expression model $f_2^{-1}$ can be obtained and utilized, any storage position and any transmission/reception method may be accepted. The conversion of an irradiation shape (x, y, z) formed by use of the inverse-map mathematical expression model $f_2^{-1}$ into the irradiation control values $(I_a, I_b, E_b)$ is performed in the same way as that in Embodiment 1 where the function $f_1$ is utilized; thus, in Embodiment 2, the method of obtaining unknown parameters in the inverse-map mathematical expression model $f_2^{-1}$ will be explained.

It is assumed that $I_a$ is a control value for the X direction scanning electromagnet 2a, $I_b$ is a control value for the Y direction scanning electromagnet 2b, $E_b$ is a control value related to the energy of a charged particle beam, and the irradiation position of a charged particle beam with which irradiation is performed is represented by (x, y, z). Provided that there exists no fluctuation of the incident point at which a charged particle beam $B_{ec}$ enters the scanning electromagnet 2a, (x, y, z) is uniquely determined when $(I_a, I_b, E_b)$ is determined. This physical phenomenon is considered as mapping from $(I_a, I_b, E_b)$ to (x, y, z). When the function (a scanning electromagnet, for example) of forming an irradiation shape is disposed at the most downstream side (directly in the vicinity of the isocenter C), this mapping can intuitively be understood and becomes simple one. Accordingly, to date, the function of forming an irradiation shape has been disposed at the most downstream side. However, in a particle beam therapy system according to the present invention, the distance between a scanning electromagnet for forming an irradiation shape and the isocenter C is made long or a deflection electromagnet is inserted between them, in order to suppress the divergence angle; therefore, in Embodiment 1, the function $f_1$ is obtained as a map through a simulation, for example. In contrast, in Embodiment 2 according to the present invention, as illustrated in FIGS. 3 and 4, there are obtained, based on actually measured values, unknown parameters in the inverse-map mathematical expression model $f_2^{-1}$ that creates irradiation control values $(I_a, I_b, E_b)$, which are anticipated from point sequence data of target irradiation coordinates (x, y, z) for forming a desired irradiation shape.

Next, a specific calibration method (an adjustment method for a particle beam therapy system) will be explained. In addition, in Embodiment 2, assuming that the main control for obtaining unknown parameters in the inverse-map mathematical expression model $f_2^{-1}$ is performed by the inverse map calculation unit 12, one example thereof will be explained by use of the flowchart in FIG. 5.

After the inverse map calculation unit 12 is activated to start the calibration (the step S10), a beam orbit is set, and there is provided the beam measurement unit 10 that measures the actual irradiation position of a charged particle beam in accordance with the set beam orbit (the step S20). Although it may be implemented manually, the setting of the beam measurement unit 10 is implemented in accordance with a command from the inverse map calculation unit 12, by providing an unillustrated apparatus that can rotate on the isocenter and makes its center axis (a line that passes through the respective centers of the beam profile monitor 10a, the beam profile monitor 10b, and the water phantom 10c) coincide with the center of the beam orbit in accordance with the set beam orbit.

Next, from the data server 9b, there is read a combination (data strings: Equation (1)) of a plurality of irradiation control values ($I_a$, $I_b$, $E_b$) that are different from one another and required for calibration (the step S100); then, along the read data string, actual irradiation (the step S110) and the measurement (the step S120) of actual irradiation position coordinates are performed sequentially (i=0 to n). Specifically, for example, the overall control section 8a transmits irradiation control values to a scanning control section 8d in order of data number (i); the scanning control section 8d controls the energy of the scanning electromagnets 2a and 2b and a charged particle beam in accordance with the irradiation control values ($I_a$, $I_b$, $E_b$) (in the case of i-th data) and actually performs trial irradiation.

$$(I_{a_0}, I_{b_0}, E_{b_0}) \quad\quad\quad (1)$$
$$(I_{a_1}, I_{b_1}, E_{b_1})$$
$$\vdots$$
$$(I_{a_n}, I_{b_n}, E_{b_n})$$

where each subscript numeral denotes the data number (in the case where the number of data items is n+1). The data strings may be stored in a memory of the irradiation control unit 8.

The measurement of actual irradiation position coordinates is performed, for example, in the following manner. By means of the beam profile monitor 10a, there are obtained the coordinates ($x_a$, $y_a$, $z_a$) of a beam, in a plane perpendicular to the beam orbit, that is $z_a$ away in the z direction from the z-direction reference point of the water phantom 10c. By means of the beam profile monitor 10b, there are obtained the coordinates ($x_b$, $y_b$, $z_b$) of a beam that is $z_b$ away in the z direction from the z-direction reference point of the water phantom 10c. When there can be obtained the depth z where a Bragg peak occurs in the water phantom 10c, the coordinates (x, y, z) where the Bragg peak occurs can be obtained. Accordingly, the actual irradiation shape ($x_i$, $y_i$, $z_i$) for i-th irradiation control values ($I_{ai}$, $I_{bi}$, $E_{bi}$) can be obtained.

By repeating such an actual measurement (the steps S110 and S120) a predetermined times (i=0 to n), there can finally be obtained the data string of the actual irradiation position coordinates (x, y, z) corresponding to the (n+1) sets of data strings, of irradiation control values ($I_a$, $I_b$, $E_b$), which are different from one another (the step S200). As described above, the conversion from the irradiation control values ($I_a$, $I_b$, $E_b$) to the actual irradiation coordinate position (x, y, z) is considered as mapping in the positive direction; therefore, by varying the irradiation control values ($I_a$, $I_b$, $E_b$) and measuring each corresponding actual irradiation coordinate position (x, y, z), an inverse map is obtained from the combination of the data string of control values and the data string of measured values.

The inverse-map mathematical expression $f_2^{-1}$ is created from the combination of the actual data strings for a plurality of (n+1) trial irradiations. A preferable example of inverse-map mathematical expression model is typified by a polynomial expression model. Equation (2) represents an example of the polynomial expression in which the highest degree is 2.

$$\begin{cases} I_{ae} = a_{000} + a_{001}x + a_{002}x^2 + a_{010}y + a_{011}xy + a_{020}y^2 + a_{100}z + \\ \quad\quad a_{101}xz + a_{110}yz + a_{200}z^2 \\ I_{be} = b_{000} + b_{001}x + b_{002}x^2 + b_{010}y + b_{011}xy + b_{020}y^2 + b_{100}z + \\ \quad\quad b_{101}xz + b_{110}yz + b_{200}z^2 \\ E_{be} = c_{000} + c_{001}x + c_{002}x^2 + c_{010}y + c_{011}xy + c_{020}y^2 + c_{100}z + \\ \quad\quad c_{101}xz + c_{110}yz + c_{200}z^2 \end{cases} \quad (2)$$

where x, y, z are coordinates of a target irradiation position; $I_{ae}$ and $I_{be}$ are estimation values of control values for the scanning electromagnet, and $E_{be}$ is an estimation value of the control value for the energy of a charged particle beam; $a_{000}$, $a_{001}$, $a_{002}$, ..., $a_{200}$, $b_{000}$, $b_{001}$, $b_{002}$, ..., $b_{200}$, $c_{000}$, $c_{001}$, $c_{002}$, ..., $c_{200}$ are coefficients (unknown parameters) that determine the characteristics of the inverse-map mathematical expression model $f_2^{-1}$.

A preferable example of obtaining the coefficients, of a polynomial expression, which are unknown parameters is typified by the least square method. Equations (3) and (4) are equations for obtaining the coefficients of a polynomial expression through the least square method.

$$\overbrace{\begin{bmatrix} 1 & x_0 & x_0^2 & y_0 & x_0 y_0 & y_0^2 & z_0 & x_0 z_0 & y_0 z_0 & z_0^2 \\ 1 & x_1 & x_1^2 & y_1 & x_1 y_1 & y_1^2 & z_1 & x_1 z_1 & y_1 z_1 & z_1^2 \\ \vdots & \vdots & \vdots & \vdots & \vdots & \vdots & \vdots & \vdots & \vdots & \vdots \\ 1 & x_n & x_n^2 & y_n & x_n y_n & y_n^2 & z_n & x_n z_n & y_n z_n & z_n^2 \end{bmatrix}}^{A_{carib}} \overbrace{\begin{bmatrix} a_{000} & b_{000} & c_{000} \\ a_{001} & b_{001} & c_{001} \\ a_{002} & b_{002} & c_{002} \\ a_{010} & b_{010} & c_{010} \\ a_{011} & b_{011} & c_{011} \\ a_{020} & b_{020} & c_{020} \\ a_{100} & b_{100} & c_{100} \\ a_{101} & b_{101} & c_{101} \\ a_{110} & b_{110} & c_{110} \\ a_{200} & b_{200} & c_{200} \end{bmatrix}}^{x} = \overbrace{\begin{bmatrix} I_{a_0} & I_{b_0} & E_{b_0} \\ I_{a_1} & I_{b_1} & E_{b_1} \\ \vdots & \vdots & \vdots \\ I_{a_n} & I_{b_n} & E_{b_n} \end{bmatrix}}^{B_{carib}} \quad (3)$$

$$X = (A_{carib}^T A_{carib})^{-1} A_{carib}^T B_{carib} \quad (4)$$

where the superscript T denotes a transposed matrix.

As mentioned above, unknown parameters in the inverse-map mathematical expression model $f_2^{-1}$ for each beam orbit can be set (the step S210).

With regard to these operations, in the case where necessary setting of parameters in a beam orbit has not been completed, the result of the determination in the step S300 becomes "No", and the next beam orbit (7b, 7c) is set (the step S20). In the case where the unknown parameters in the inverse-map mathematical expression model $f_2^{-1}$ for each beam orbit can be obtained, the result of the determination in the step S300 becomes "Yes", and the calibration is completed (the step S400).

After the unknown parameters (coefficients in a polynomial expression) in the inverse-map mathematical expression model $f_2^{-1}$ are obtained through the calibration, treatment irradiation is implemented. Firstly, by means of a beam monitor (unillustrated) provided in the beam transport duct 1, it is confirmed that the incident point at which a beam enters the scanning electromagnet 2a has not changed since the calibration was performed. In this situation, in the case where it is determined that the incident point of a beam has changed, the foregoing calibration procedure may be resumed so as to obtain the coefficients again. Next, the target irradiation position coordinates for each beam orbit are read from the treatment plan apparatus (the step S500). The target irradiation position coordinates may also be the data string of $(x_0, y_0, z_0), \ldots, (x_m, y_m, z_m)$ as represented in Equation (1). For example, the target irradiation position coordinates are set in order of the data number (the step S510); then, by utilizing the unknown parameters, in the inverse-map mathematical expression model $f_2^{-1}$, which have been selected in accordance with a beam orbit, the irradiation control values $(I_{aj}, I_{bj}, E_{bj})$ (in the case of j-th irradiation control values) are created (the step S520). After that, irradiation is performed based on the created control values (the step S530). By sequentially performing the foregoing procedure for the necessary points (m+1), there can be performed irradiation in which the target irradiation position set for each beam orbit is accurately reproduced.

As described above, the particle beam therapy system according to Embodiment 2 is configured in such a way that, in accordance with the beam orbit (7a, 7b, 7c), there is utilized the inverse-map mathematical expression model $f_2^{-1}$ for creating the irradiation control value estimation values $(I_{ae}, I_{be}, E_{be})$, based on (three-dimensional) irradiation control values $(I_a, I_b, E_b)$ including control values $(I_a, I_b)$ for the scanning electromagnets 2a and 2b and energy control value $E_b$ for a charged particle beam $B_{ec}$ and on the measurement values (x, y, z) of actual irradiation position coordinates at the isocenter C at a time when trial irradiation is performed with the charged particle beam $B_{ec}$ controlled through the three-dimensional irradiation control values, i.e., actual data; therefore, even in the case of a complicated system in which the scanning electromagnet is not situated at the most downstream position and the orbit between the scanning electromagnets 2a and 2b and the isocenter C varies, accurate irradiation onto a diseased site can be performed.

Moreover, in the adjustment method for a particle beam therapy system according to Embodiment 2, there are included a step (the step S20) of providing the beam measurement unit 10 that sets a beam orbit and measures the actual irradiation position coordinates (x, y, z) of a charged particle beam $B_{ec}$ in accordance with the set beam orbit (7a, 7b, 7c); a step (the step S100) of reading a plurality of irradiation control values (data strings), which are irradiation control values $(I_a, I_b, E_b)$ that include two-dimensional control values $(I_a, I_b)$ for the scanning electromagnets 2a and 2b and a control value $E_b$ for the energy of the charged particle beam $B_{ec}$ and are different from one another; a step (the steps S110 and S120) of performing actual irradiation with a charged particle beam $B_{ec}$ in accordance with the read irradiation control values and measuring the actual irradiation position coordinates (x, y, z) of the charged particle beam $B_{ec}$ at the isocenter C; and a step (the step S210) of setting unknown parameters in the inverse-map mathematical expression model $f_2^{-1}$, based on the combination of a plurality of measurement results (data strings) for actual irradiation position coordinates and a plurality of corresponding irradiation control values (data strings). As a result, there can be obtained a particle beam therapy system that enables accurate irradiation for each beam orbit.

Still moreover, the particle beam therapy system according to Embodiment 2 is configured in such a way as to include the inverse map calculation unit 12 that implements a step (the step S100) of reading a plurality of irradiation control values (data strings), which are irradiation control values $(I_a, I_b, E_b)$ that include two-dimensional control values $(I_a, I_b)$ for the scanning electromagnets 2a and 2b and a control value $E_b$ for the energy of the charged particle beam $B_{ec}$ and are different from one another; a step (the step S120) of measuring the actual irradiation position coordinates (x, y, z) at the isocenter C of the charged particle beam $B_{ec}$ with which actual irradiation has been performed in accordance with the read irradiation control values; and a step (the step S210) of setting unknown parameters in the inverse-map mathematical expression model $f_2^{-1}$, based on the combination of a plurality of measurement results (data strings) for actual irradiation position coordinates and a plurality of corresponding irradiation control values. As a result, high-flexibility and accurate irradiation can continuously be performed.

In addition, in Embodiment 2, there is provided a function in which, when actual data at a time of calibration is given to the inverse map calculation unit 12, coefficients (unknown parameters) in a polynomial expression is calculated through the least square method; however, the calculation function may be provided in another unit such as the irradiation control unit 8 or the irradiation plan commanding unit 9.

The degree of the polynomial expression model may be changed depending on the characteristics of a particle beam irradiation system to be dealt with; the degree may appropriately be raised when the nonlinearity of the particle beam irradiation system is high. Accordingly, a degree of a polynomial expression model may not be the same as that of the polynomial expression model, represented in Equation (2), having the highest degree of 2. In Embodiment 2 of the present invention, some polynomial expression models are preliminarily prepared so that an operator can select a polynomial expression model. For example, in Equation (2) above, x, y, z are equally dealt with; however, because contribution of z for x and y is less than that of x or y for x and y, there may also be provided a polynomial expression model in which, in order to reduce the amount of calculation processing, the degree of z for x and y is decreased compared with that of x or y so that this polynomial expression model is selected as may be necessary.

In Embodiment 2, there has been explained a case where (n+1) data strings covers the irradiation region for a single beam orbit; however, in the case where correction is applied to an orbit that has been calibrated once, the number of measurement points may appropriately be reduced.

A method of dividing an irradiation area into a number of sub-areas and obtaining a map for each sub-area is also effective, especially in the case where the nonlinearity is high. In this case, the irradiation control unit 8 may perform switching to unknown parameters to be utilized based on read irradiation position coordinates or may perform switching among inverse-map mathematical expression models themselves (for example, switching the degree of a polynomial expression).

Variant Example of Embodiment 2

Figure 6:
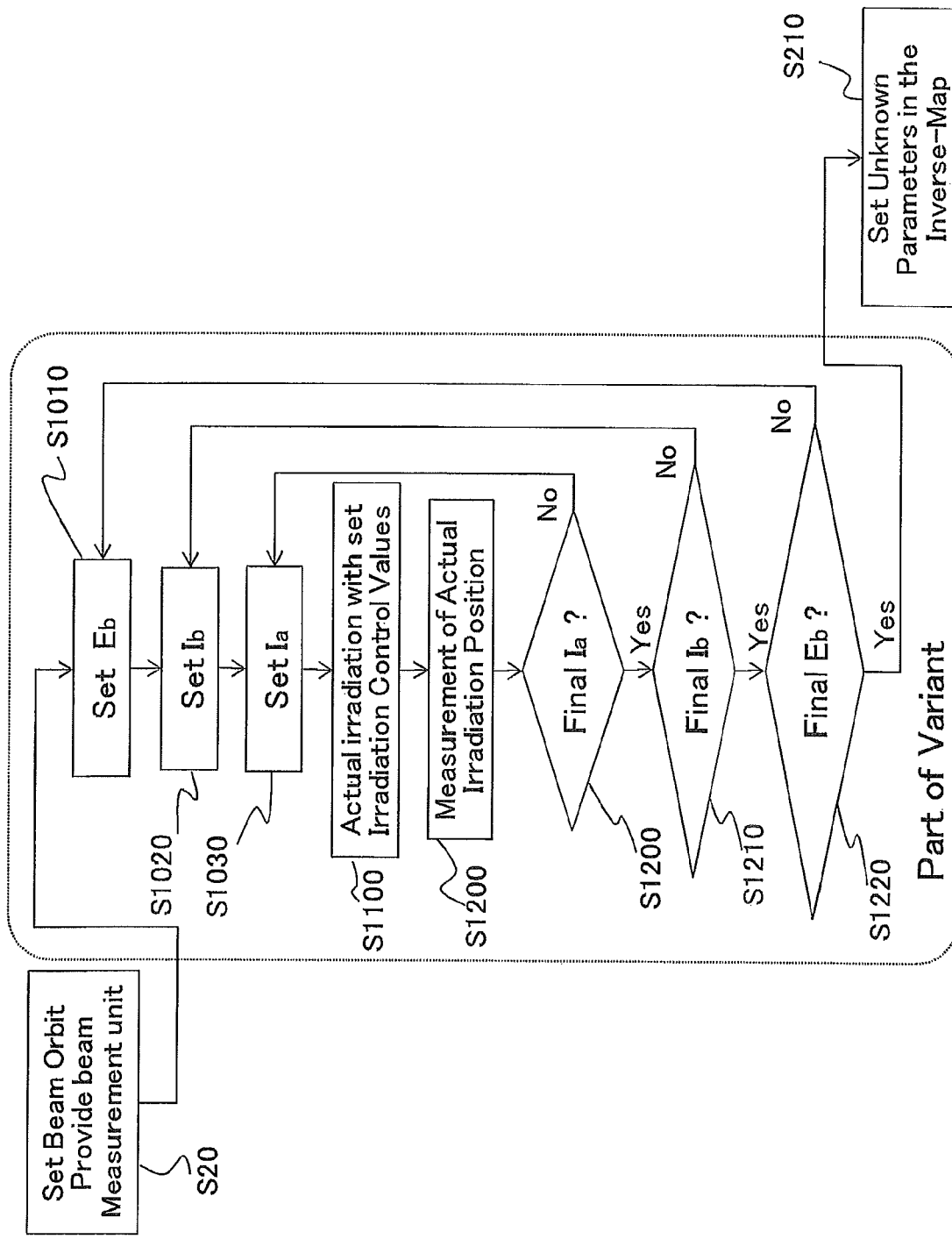
FIG. 6 is a flowchart representing an adjustment method for a variant example of the particle beam therapy system according to Embodiment 2 of the present invention.

In Embodiment 2, there has been described an example where irradiation control values are read as a data string when calibration is implemented, and actual irradiation is performed for the read data string (the steps S100 through S200 in FIG. 5); however, in the case where the respective variants of the control values are changed every interval, calibration may be implemented according to the sequence represented in FIG. 6. FIG. 6 is a flowchart representing an example in which the process corresponding to the steps S100 through S200 in FIG. 5 has been varied; because being the same as processes in FIG. 5, the process before the step S20 and the process after the step S210 are omitted.

In the first place, the energy control value $E_b$, for a charged particle beam $B_{ec}$, which mainly effects the z direction (the depth) is set to an initial value (e.g., $E_{b1}$ in $E_{b1}, E_{b2}, \ldots, E_{br}$) (the step S1010). Next, the control value $I_b$ of the scanning electromagnet $2_b$ is set to an initial value (e.g., $I_{b1}$ in $I_{b1}, I_{b2}, \ldots, I_{bq}$) (the step S1020). Next, the control value $I_a$ of the scanning electromagnet $2a$ is set to an initial value (e.g., $I_{a1}$ in $I_{a1}, I_{a2}, \ldots, I_{ap}$) (the step S1030). After that, actual irradiation is performed with the set irradiation control values (the step S1100), and the actual irradiation position coordinates (x, y, z) in the vicinity of the isocenter C are measured.

In the case where the respective required numbers of settings for each control value have not been completed in the steps S1200 through S1220, the control values are set to the following respective values ($I_{a2}, \ldots, I_{ap}/I_{b2}, \ldots, I_{bq}/E_{b2}, \ldots, E_{br}$) (the steps S1030, S1020, and S1010), and when the values sequentially increase (for example, it is assumed that the respective control values change with the same increment in the strings $I_{a2}, \ldots, I_{ap}/I_{b2}, \ldots, E_{br}$), there can be obtained a combination of the data strings of (p×q×r) three-dimensional-lattice irradiation control values ($I_a, I_b, E_b$) and the data strings of irradiation shape (x, y, z) (the step S1220). Then, based on the foregoing data combination, the unknown parameters in the inverse-map mathematical expression model $f_2^{-1}$ can be set through the least square method (the step S210).

In the variant example of Embodiment 2, a series of measurement is performed in such a way that while two variables are kept constant, one variable ($I_a$, in this example) is changed; therefore, when the irradiation depth is measured by means of a water phantom, the dose sensor can readily keep track of a position where a Bragg peak occurs, whereby the actual irradiation position coordinates can efficiently be measured.

In the foregoing variant example, there has been explained a case where there is obtained fine and approximately lattice-shaped data (p×q×r points) that covers the irradiation region for a beam orbit; however, in the case where correction is applied to an orbit that has been calibrated once, the number of measurement points may appropriately be reduced. For example, the respective increments of the control values may be increased so that the net becomes coarse. Alternatively, an irradiation area may be divided into a number of sub-areas. In this case, the respective increments, the starting points, and the ending points of the variables are determined; therefore, it becomes easier to visually understand how the number of measurement points is reduced (whether the accuracy is lowered or the area is reduced).

Embodiment 3

Figure 7:
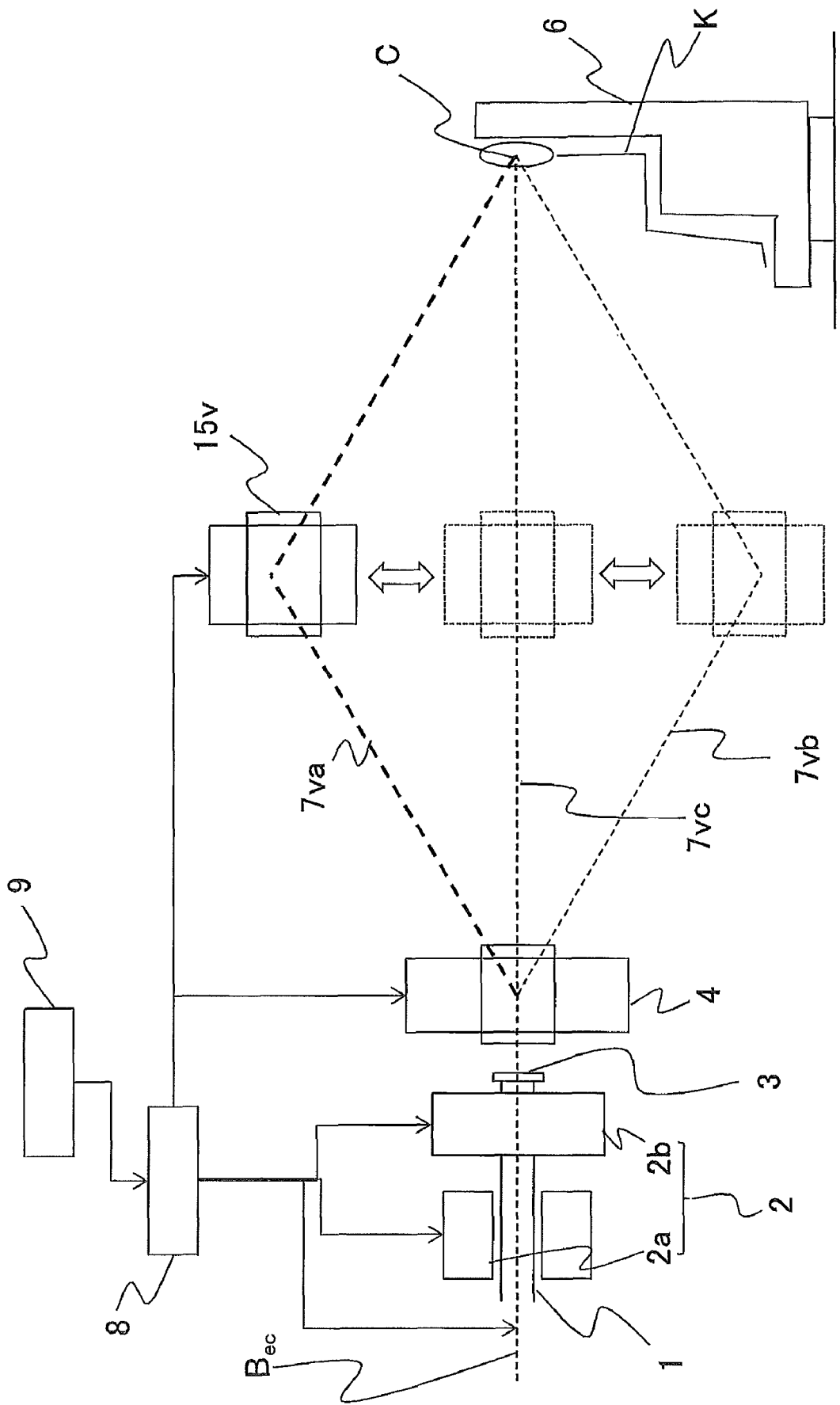
FIG. 7 is a diagram illustrating the configuration of a particle beam therapy system according to Embodiment 3 of the present invention.
Figure 8:
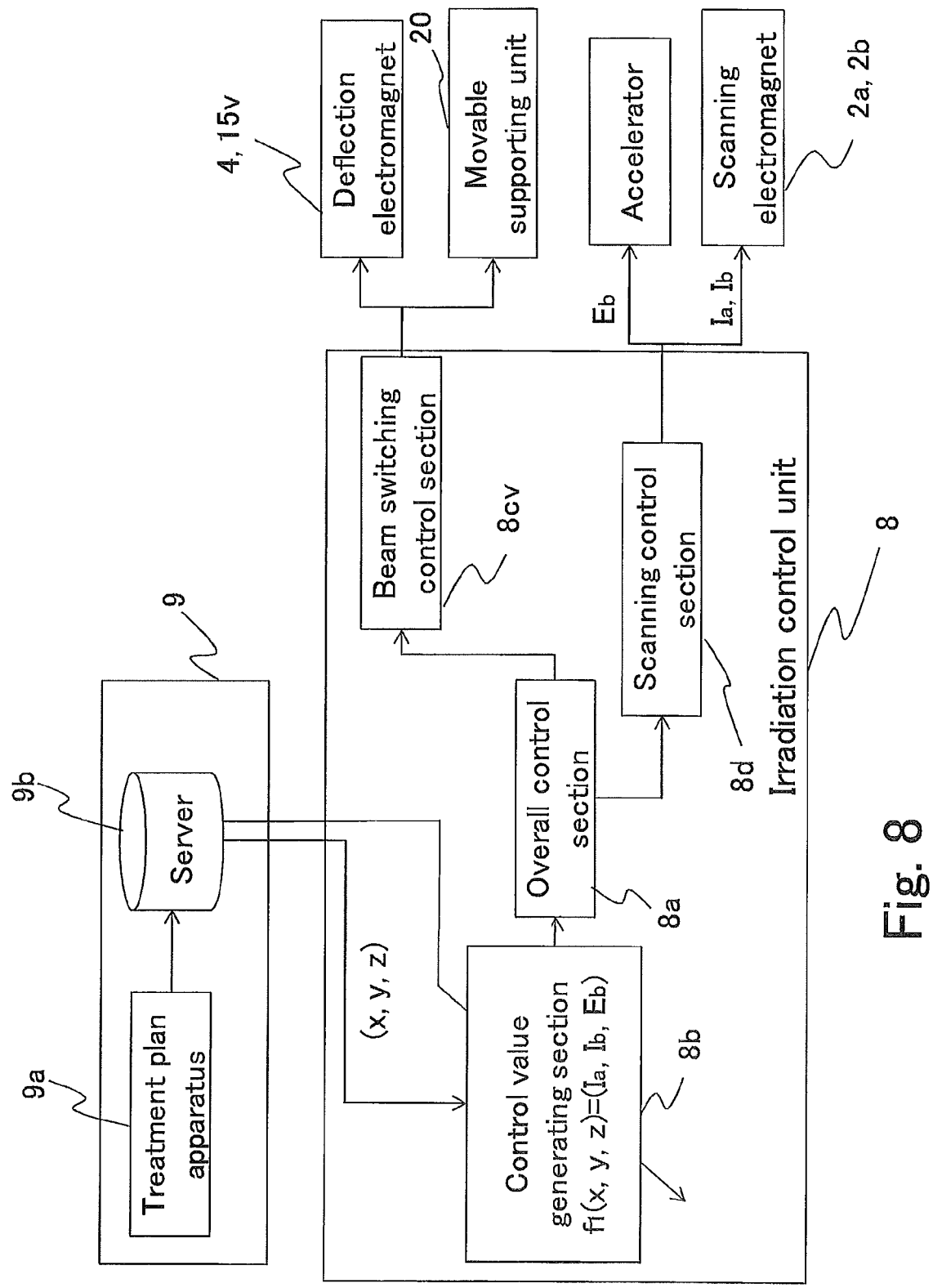
FIG. 8 is a block diagram illustrating the functions of a particle beam therapy system according to Embodiment 3 of the present invention.

In Embodiments 2 and 3, there has been described a case where a plurality of beam orbits is provided at the downstream side of the scanning electromagnet 2, switching among charged particle beams can be performed by the deflection electromagnet 4 that switches beam orbits, and there is provided the necessary deflection electromagnet 5a or 5b for each beam orbit. In Embodiment 3, the deflection electromagnet is made movable along a beam orbit so that a plurality of beam orbits is dealt with by a single deflection electromagnet. FIGS. 7 and 8 are diagrams for explaining a particle beam therapy system according to Embodiment 3 of the present invention; FIG. 7 is a diagram illustrating the configuration of a particle beam therapy system; FIG. 8 is a block diagram illustrating the function thereof; a deflection electromagnet 15v can move in accordance with a beam orbit 7v. Other parts are the same as those in Embodiment 1 or Embodiment 2.

Although unillustrated in FIG. 7, the deflection electromagnet 15v is movably provided on a movable supporting unit; as illustrated in FIG. 8, in the case where beam orbits are switched, based on a command from a beam switching control section 8cv, the deflection electromagnet 15v is moved to an optimum position in accordance with a selected beam orbit 7v.

In other words, in Embodiment 3, the deflection electromagnet 15v is made movable so that the deflection electromagnet 15v can commonly be utilized in a plurality of beam orbits 7v. In this case, only the deflection electromagnet 15v is the unit whose position per se moves when the irradiation angle is changed, and the deflection electromagnet 15v is sufficiently far from a patient; therefore, the method according to Embodiment 3 readily enables remote multi-port irradiation to be performed.

The method, described in Embodiment 2, in which adjustment is performed by use of the inverse-map mathematical expression model $f_2^{-1}$ can be applied also to Embodiment 3.

As described above, the particle beam therapy system according to Embodiment 3 is configured in such a way that the deflection electromagnets for switching beam orbits are provided at the downstream side of the scanning electromagnet 2, and that there are provided the beam switching electromagnet 4, which is a first deflection electromagnet, that deflects a charged particle beam $B_{ec}$ scanning-outputted from the scanning electromagnet 2, in accordance with a selected orbit 7v; and the deflection electromagnet 15v, which is a third deflection electromagnet, that is provided at the downstream of the beam switching deflection electromagnet 4, that moves in accordance with the selected beam orbit 7v, and that deflects a charged particle beam $B_{ec}$ that has been deflected by the beam switching deflection electromagnet 4 toward the isocenter C. As a result, by driving the deflection electromagnet 15v for deflecting a beam orbit, a single deflection electromagnet can commonly be utilized in a plurality of deflection electromagnets; thus, even in the case where the respective numbers of the deflection electromagnets and the driving power sources therefor are small, the effects described in Embodiments 1 and 2 can be demonstrated.

In FIG. 7, there is illustrated only a state where the deflection electromagnet 15v moves upward or downward in the plane of the paper; however, the deflection electromagnet 15v may be moved in the direction perpendicular to the plane of the paper. In this situation, the deflection direction of the deflection electromagnet 4 may also be slanted as may be necessary.

Figure 9:
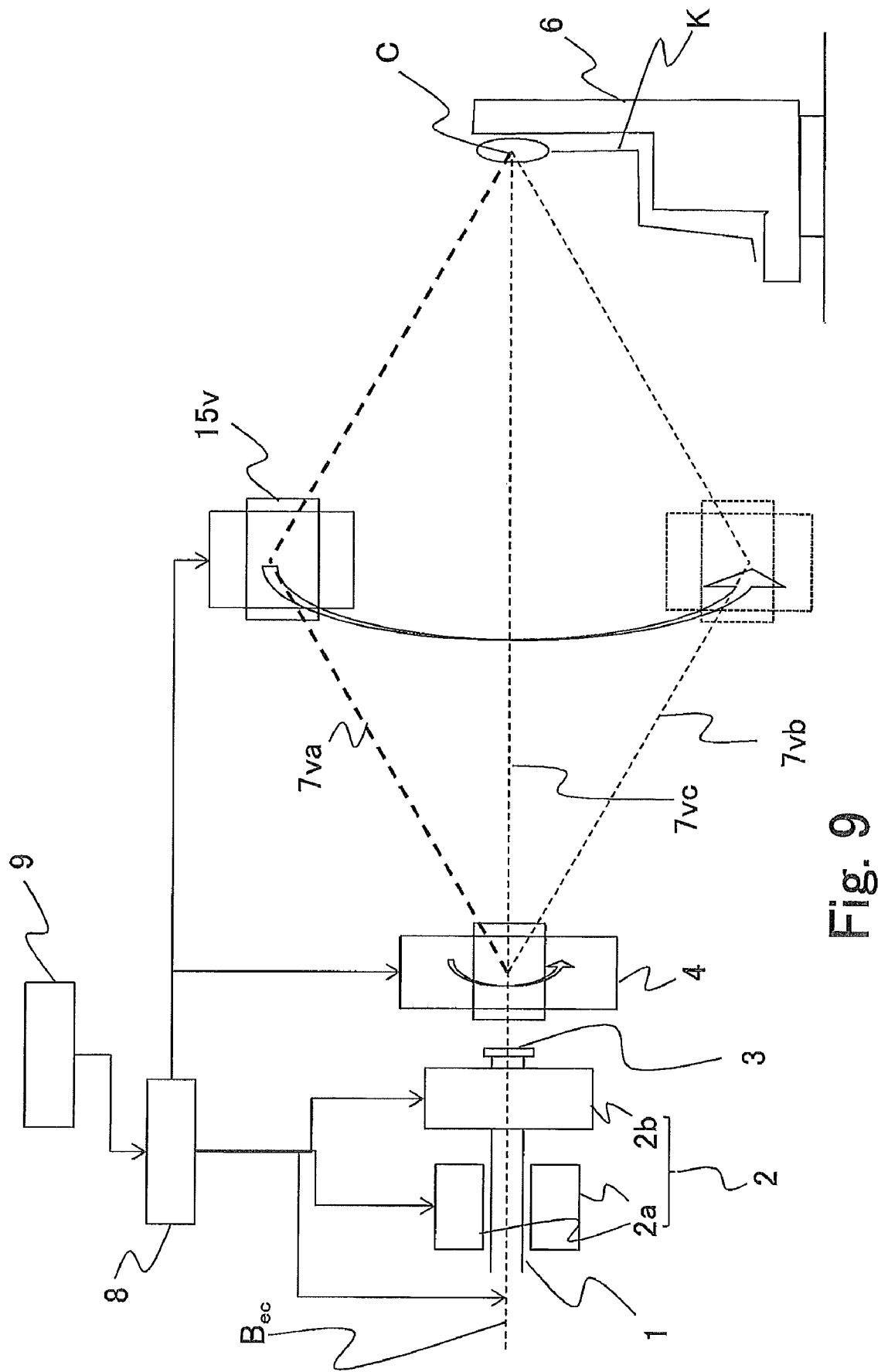
FIG. 9 is a diagram illustrating the configuration of a variant example of the particle beam therapy system according to Embodiment 3 of the present invention.

Moreover, as illustrated in a variant example in FIG. 9, the deflection electromagnet 15v may revolve around the beam orbit 7vc. In this case, the deflection electromagnet 4 may revolve around the beam orbit 7vc in conjunction with the movement of the deflection electromagnet 15v.

Embodiment 4

Figure 10:
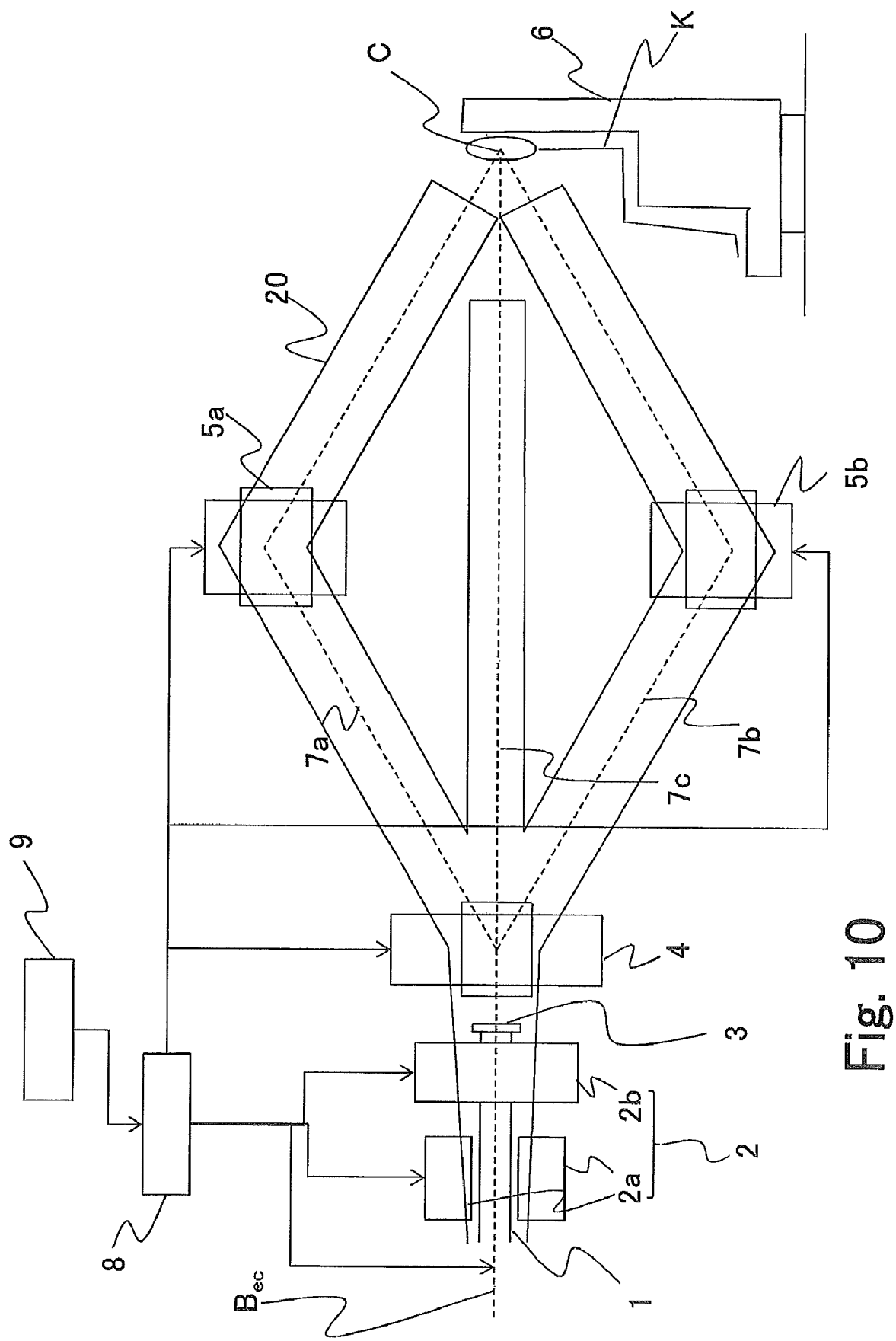
FIG. 10 is a diagram illustrating the configuration of a particle beam therapy system according to Embodiment 4 of the present invention.

In Embodiment 1, there has been described a case where a plurality of beam orbits is provided at the downstream side of the scanning electromagnet 2, switching among beams orbits can be performed by the deflection electromagnet 4 that switches beam orbits, and there is provided the necessary deflection electromagnet 5 for each beam orbit; however, in a particle beam therapy system according to Embodiment 4, a beam transport duct 20 is provided for each beam orbit, as illustrated in FIG. 10. Other functions and configurations are the same as those in Embodiment 1; thus, explanations therefor will be omitted.

The purpose of providing the beam transport duct 20 is to suppress the phenomenon that, due to passing through the air, a charged particle beam $B_{ec}$ diffuses and hence the beam spot size is enlarged. In a scanning irradiation type particle beam therapy system, irradiation onto a tumor volume, which is an irradiation subject, is performed in the step of a sub-area; therefore, it is required to suppress the beam spot size to be smaller than approximately several millimeters. Thanks to the beam transport duct 20, the beam orbit can be kept vacuum or helium-gaseous; therefore, a charged particle beam can be suppressed from diffusing (different from diverging due to scanning).

Even in the case where the duct is capable of communicating with the outer air, there can be provided a protection function of preventing a foreign material or a person from entering the orbit of a charged particle beam.

The method, described in Embodiment 2, in which the inverse-map mathematical expression model $f_2^{-1}$ is utilized can be applied also to Embodiment 4; thus, because the effect of the outer air is suppressed, more accurate adjustment can be performed.

As described above, between the first deflection electromagnet 4 and the isocenter C, there is provided the beam transport duct 20 for each of the plurality of beam orbits; therefore, because the orbit of a charged particle beam can be kept vacuum or helium-gaseous, there can be obtained a particle beam therapy system that can perform irradiation with a beam whose spot size is sufficiently small, e.g., approximately several millimeter, which is suitable for spot-scanning.

Embodiment 5

Figure 11:
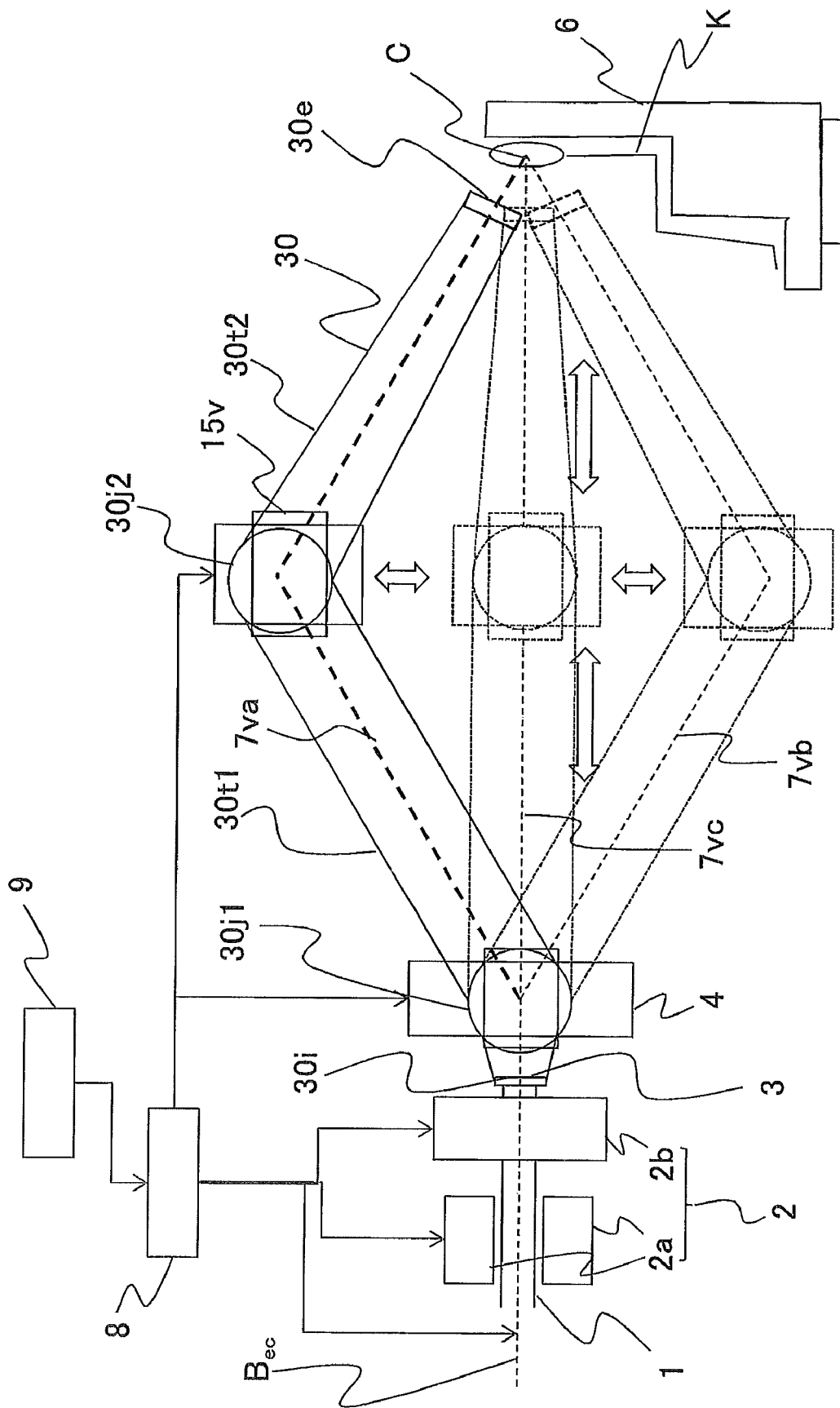
FIG. 11 is a diagram illustrating the configuration of a particle beam therapy system according to Embodiment 5 of the present invention.

In Embodiment 3, there has been described a case where a plurality of beam orbits is provided at the downstream side of the scanning electromagnet 2, switching among beams orbits can be performed by the deflection electromagnet 4 that switches beam orbits, and the deflection electromagnet 15v is moved in accordance with a selected beam orbit; however, in a particle beam therapy system according to Embodiment 5, as illustrated in FIG. 11, there is provided a beam transport duct 30 capable of moving or being deformed while moving in accordance with a set bean orbit. Other functions and configurations are the same as those in Embodiment 3; thus, explanations therefor will be omitted.

The beam transport duct 30 is configured with a beam feed port 30i connected with the beam outlet window 3, a beam emitting port 30e that is disposed in the direct vicinity of the isocenter and outputs a charged particle beam toward the isocenter C, a joint portion 30j1 disposed at a position corresponding to the deflection electromagnet 4, a moving joint portion 30j2 that moves in conjunction with the movement of the deflection electromagnet 15v, a straight duct portion 30t1 that connects the joint portion 30j1 with the joint portion 30j2, and a straight duct portion 30t2 that connects the joint portion 30j2 with the beam emitting port 30e; each of the straight duct portions 30t1 and 30t2 can change a connection angle at which it and the corresponding joint portion are connected with each other, and can change its length (shape) while keeping its linearity. By airtightly bonding the joint portion with the straight duct portion, the inside of the beam transport duct 30 can be kept vacuum or helium-gaseous.

Figure 12:
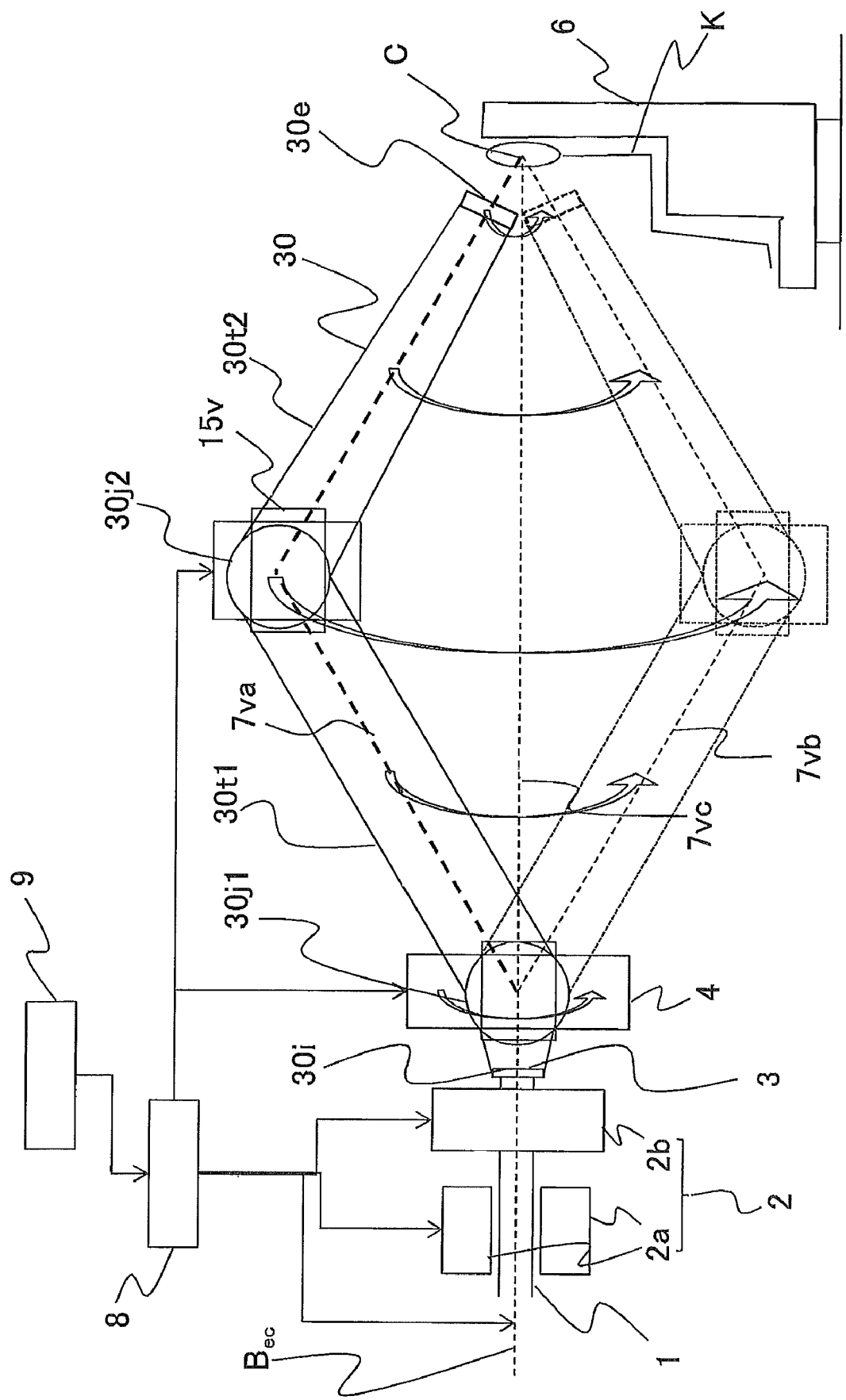
FIG. 12 is a diagram illustrating the configuration of a variant example of the particle beam therapy system according to Embodiment 5 of the present invention.

The beam transport duct 30, according to Embodiment 5, which can move or can be deformed while moving in conjunction with the deflection electromagnet 15v can be applied also to a case where, as is the case with the variant example of Embodiment 3, the deflection electromagnet 15v moves while revolving. FIG. 12 illustrates the configuration of a particle beam therapy system where there is provided a beam transport duct 30 that can move or can be deformed while moving in conjunction with the revolution of the deflection electromagnet 15v; the operation thereof is the same as that illustrated in FIG. 11; therefore, the explanation therefor will be omitted.

The method, described in Embodiment 2, in which the inverse-map mathematical expression model $f_2^{-1}$ is utilized can be applied also to Embodiment 5; thus, because the effect of the outer air is suppressed, more accurate adjustment can be performed.

As described above, between the first deflection electromagnet 4 and the isocenter C, there is provided the beam transport duct 30 that moves or that is deformed while moving in accordance with each selected beam orbit; therefore, because the beam orbit can be kept vacuum or helium-gaseous, there can be obtained a particle beam therapy system that can perform irradiation with a beam whose spot size is sufficiently small, e.g., approximately several millimeter, which is suitable for spot-scanning.

DESCRIPTION OF REFERENCE NUMERALS 1 beam transport duct
2 scanning electromagnet:
   2a X direction scanning electromagnet
   2b Y direction scanning electromagnet
3 beam outlet window
4 beam switching deflection electromagnet (first deflection electromagnet)
5 deflection electromagnet (second deflection electromagnet)
   5a deflection electromagnet (for beam orbit 7a)
   5b deflection electromagnet (for beam orbit 7b)
15v deflection electromagnet (moving type)
6 chair-type patient holding apparatus
7 beam orbit: 7a, 7va, 7b, 7vb, 7c, 7vc
8 irradiation control unit
9 irradiation plan commanding unit
10 beam measurement unit
   10a, 10b beam profile monitor
   10c water phantom
20, 30 beam transport duct
C isocenter
$f_1$ function
$f_2^{-1}$ inverse-map mathematical expression model
$I_a, I_b, E_b$ control value:
   $(I_a, I_b, E_b)$ irradiation control value
(x, y, z) irradiation position coordinates

The invention claimed is:

1. A particle beam therapy system, comprising:
   a scanning electromagnet provided with two scanning electromagnets that perform control to scan a supplied charged particle beam in respective different directions so that the charged particle beam is formed in a three-dimensional irradiation shape based on a treatment plan; and
   a deflection electromagnet that switches orbits for a charged particle beam in such a way that the charged particle beam with which scanning is performed by the scanning electromagnet heads for an isocenter through a single beam orbit selected from a plurality of beam orbits for multi-port irradiation established between the isocenter and the scanning electromagnet,
   wherein the deflection electromagnet includes a first deflection electromagnet that is provided at the downstream side of the scanning electromagnet and deflects a charged particle beam with which scanning has been performed by the scanning electromagnet, in accordance with the selected orbit; and a second deflection electromagnet that is provided at the downstream side of the first deflection electromagnet and deflects to the isocenter a charged particle beam that has been deflected by the first deflection electromagnet.

2. The particle beam therapy system according to claim 1, wherein the first deflection electromagnet is a beam switching electromagnet.

3. The particle beam therapy system according to claim 1, wherein the second deflection electromagnet includes respective deflection electromagnets provided for the plurality of beam orbits.

4. The particle beam therapy system according to claim 3, further including, between the first deflection electromagnet and the isocenter C, a beam transport duct for each of the plurality of beam orbits.

5. The particle beam therapy system according to claim 1, wherein the second deflection electromagnet is a deflection electromagnet that moves in accordance with a selected beam orbit.

6. The particle beam therapy system according to claim 5, further including, between the first deflection electromagnet and the isocenter C, a beam transport duct that moves or that is deformed while moving in accordance with the selected beam orbit.

7. The particle beam therapy system according to claim 1, further including an irradiation control unit that converts irradiation position coordinates for forming the three-dimensional irradiation shape, by use of a function set in accordance with the selected beam orbit, and controls the energy of the scanning electromagnet and the charged particle beam by utilizing control values obtained through the conversion.

8. The particle beam therapy system according to claim 7, wherein, as the function set in accordance with the beam orbit, there is utilized an inverse-map mathematical expression model for performing conversion to irradiation control values from irradiation position coordinates obtained based on irradiation control values including two-dimensional control values for the scanning electromagnet and a control value for the energy of the charged particle beam and on measurement values of actual irradiation position coordinates, at the isocenter, of the charged particle beam controlled by use of the irradiation control values.

9. The particle beam therapy system according to claim 8, further including an inverse map calculation unit that performs a step of reading a plurality of irradiation control values that are different from one another; a step of measuring the actual irradiation position coordinates, at the isocenter, of a charged particle beam that has been actually irradiated in accordance with the read irradiation control values; and a step of setting unknown parameters in the inverse-map mathematical expression model, based on a combination of a plurality of measurement results for the measured actual irradiation position coordinates and the plurality of irradiation control values.

10. An adjustment method for a particle beam therapy system, comprising:

setting, by an irradiation control unit of the particle beam therapy system, a beam orbit and providing a beam measurement unit that measures the irradiation position coordinates of a charged particle beam irradiated from the particle beam therapy system in accordance with the set beam orbit;

reading, by the irradiation control unit, a plurality of irradiation control values that are different from one another;

irradiating, by the irradiation control unit, a charged particle beam onto the beam measurement unit in accordance with the read irradiation control values and measuring the irradiation position coordinates of the charged particle beam; and setting, by the irradiation control unit, unknown parameters in an inverse-map mathematical expression model, based on a combination of a plurality of measurement results for the measured irradiation position coordinates and the plurality of irradiation control values.

* * * * *